(12) United States Patent
Yamada et al.

(10) Patent No.: US 12,076,724 B2
(45) Date of Patent: Sep. 3, 2024

(54) SPECIMEN PROCESSING APPARATUS, SPECIMEN MEASUREMENT SYSTEM AND METHOD FOR PROCESSING SPECIMEN

(71) Applicant: SYSMEX CORPORATION, Kobe (JP)

(72) Inventors: Kazuhiro Yamada, Kobe (JP); Kazuki Asao, Kobe (JP); Keisuke Kuwano, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 963 days.

(21) Appl. No.: 16/998,040

(22) Filed: Aug. 20, 2020

(65) Prior Publication Data
US 2021/0053050 A1 Feb. 25, 2021

(30) Foreign Application Priority Data
Aug. 23, 2019 (JP) .................. 2019-153282

(51) Int. Cl.
| | | |
|---|---|---|
| *B01L 3/00* | (2006.01) | |
| *B01L 9/06* | (2006.01) | |
| *G01N 21/01* | (2006.01) | |
| *G01N 21/64* | (2006.01) | |
| (Continued) | | |

(52) U.S. Cl.
CPC .............. *B01L 3/5085* (2013.01); *B01L 9/06* (2013.01); *G01N 21/01* (2013.01);
(Continued)

(58) Field of Classification Search
CPC .... B01L 3/5085; B01L 9/06; B01L 2200/025; B01L 2200/143; B01L 2300/0627;
(Continued)

(56) References Cited

U.S. PATENT DOCUMENTS

| | | |
|---|---|---|
| 5,416,329 A | 5/1995 | Sonne et al. |
| 9,753,048 B2 | 9/2017 | Sasaki et al. |
| (Continued) | | |

FOREIGN PATENT DOCUMENTS

| | | | |
|---|---|---|---|
| EP | 3520897 A1 | 8/2019 | |
| JP | 2009180607 A * | 8/2009 | ........... G01N 35/026 |
| (Continued) | | | |

OTHER PUBLICATIONS

Translation of JP 2009180607 A, Nakamura Mizuki, Aug. 13, 2009 (Year: 2009).*

(Continued)

*Primary Examiner* — Samuel P Siefke
*Assistant Examiner* — Henry H Nguyen
(74) *Attorney, Agent, or Firm* — METROLEX IP LAW GROUP, PLLC; Robert L. Scott, Esq

(57) ABSTRACT

A specimen processing apparatus performs processing on a specimen contained in a container. The specimen processing apparatus includes: holders having different shapes, each of the holders being configured to hold the container; a holder placement unit that comprises holder receiving portions having different shapes, the shapes of the holder receiving portions corresponding to the shapes of the holders; and a specimen processing unit that performs processing on the specimen contained in the container held by one of the holders placed on the holder placement unit.

9 Claims, 21 Drawing Sheets

(51) Int. Cl.
*G01N 21/85* (2006.01)
*G01N 33/49* (2006.01)

(52) U.S. Cl.
CPC ......... *G01N 21/6428* (2013.01); *G01N 21/85* (2013.01); *G01N 33/4915* (2013.01); *B01L 2200/025* (2013.01); *B01L 2200/143* (2013.01); *B01L 2300/0627* (2013.01); *G01N 2021/6439* (2013.01); *G01N 2201/06113* (2013.01); *G01N 2201/0633* (2013.01); *G01N 2201/0636* (2013.01)

(58) Field of Classification Search
CPC . B01L 3/5453; B01L 2300/021; G01N 21/01; G01N 21/6428; G01N 21/85; G01N 33/4915; G01N 2021/6439; G01N 2201/06113; G01N 2201/0633; G01N 2201/0636; G01N 2035/00772; G01N 2035/0494; G01N 35/04; G01N 35/00732; G01N 35/00; G01N 21/6486; G01N 35/0092; G01N 35/02; G01N 2035/00495; G01N 2035/00752; G01V 8/10

See application file for complete search history.

(56) References Cited

U.S. PATENT DOCUMENTS

| | | |
|---|---|---|
| 2010/0166606 A1 | 7/2010 | Koike et al. |
| 2011/0036450 A1 | 2/2011 | Carlsson et al. |
| 2011/0143947 A1 | 6/2011 | Chamberlin et al. |
| 2015/0298131 A1* | 10/2015 | Fox .......................... B01L 9/06 422/562 |
| 2017/0023561 A1* | 1/2017 | Martinell Gispert-Sauch ............ G01N 35/00029 |
| 2017/0059597 A1 | 3/2017 | Huber et al. |
| 2017/0315145 A1 | 11/2017 | Birrer et al. |
| 2017/0328926 A1 | 11/2017 | Sasaki et al. |
| 2018/0207549 A1* | 7/2018 | Song .................... B65D 1/0223 |

FOREIGN PATENT DOCUMENTS

| | | |
|---|---|---|
| JP | 2010-156624 A | 7/2010 |
| JP | 2013-500496 A | 1/2013 |
| JP | 2017-044698 A | 3/2017 |
| WO | 2011/148897 A1 | 12/2011 |
| WO | 2017/145556 A1 | 8/2017 |

OTHER PUBLICATIONS

Extended European search report (EESR) issued on Jan. 20, 2021 in a counterpart European patent application.
Office Action issued on Mar. 28, 2023 in a counterpart Japanese patent application.
Communication pursuant to Article 94(3) EPC issued on Jul. 15, 2022 in a counterpart European patent application.
Office Action issued on Sep. 26, 2023 in a counterpart Japanese patent application.
Communication pursuant to Article 94(3) EPC issued on Aug. 21, 2023 in a counterpart European patent application.

* cited by examiner

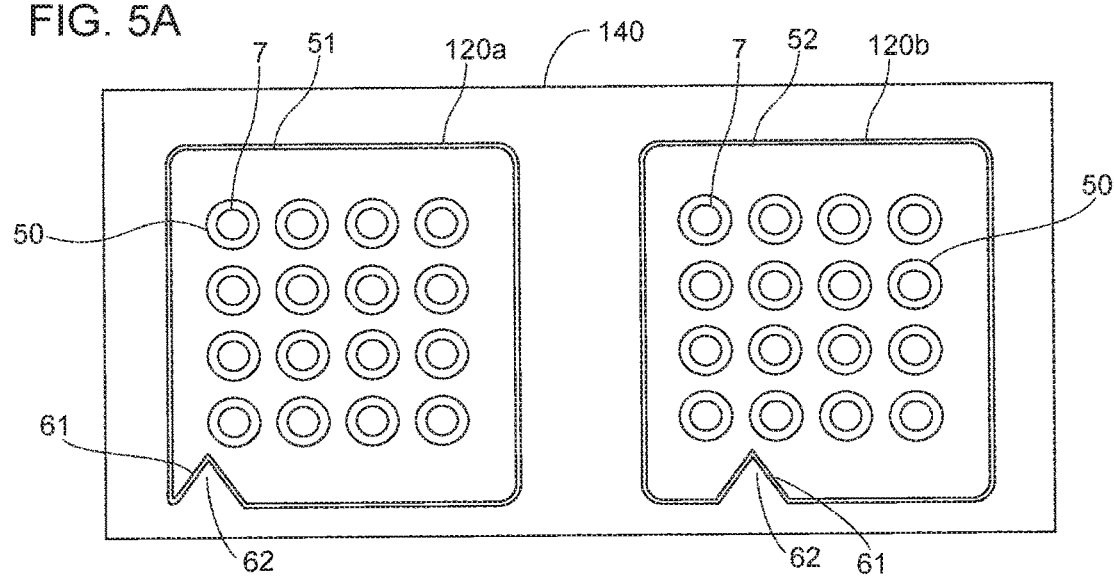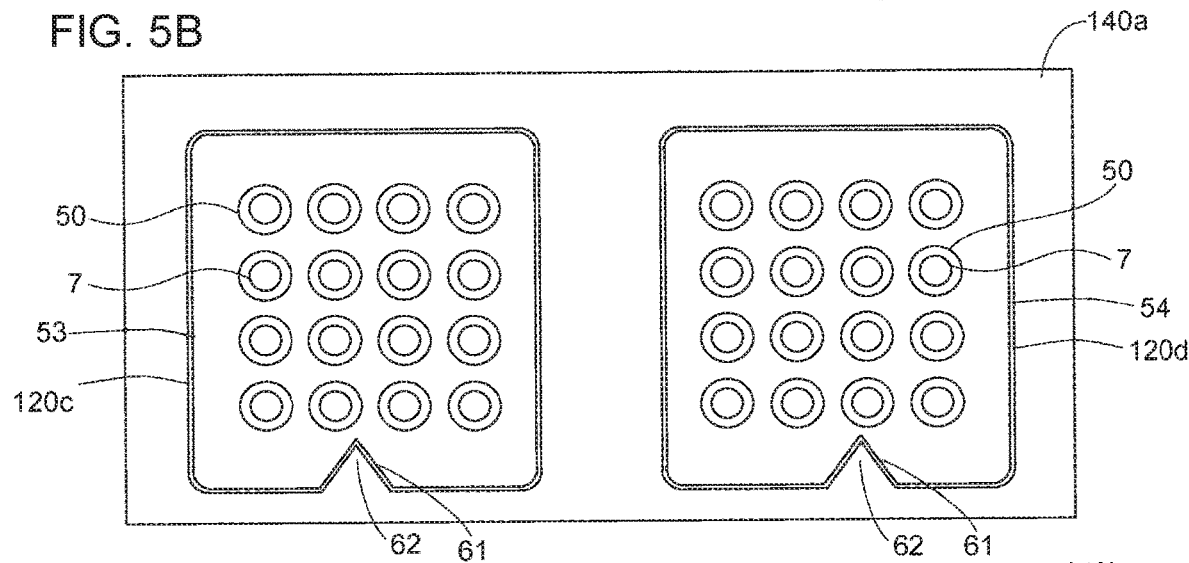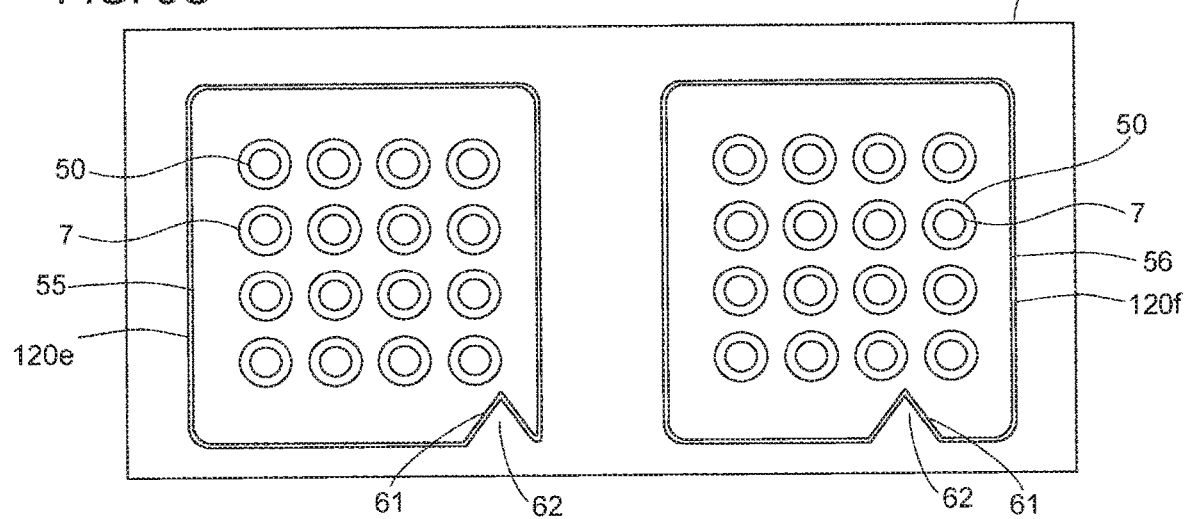

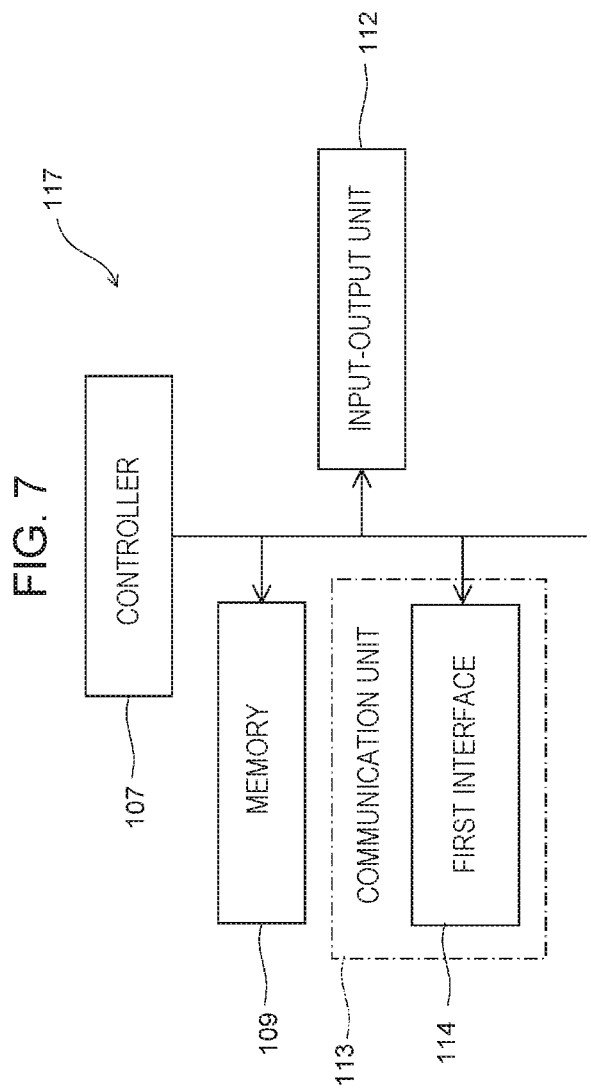

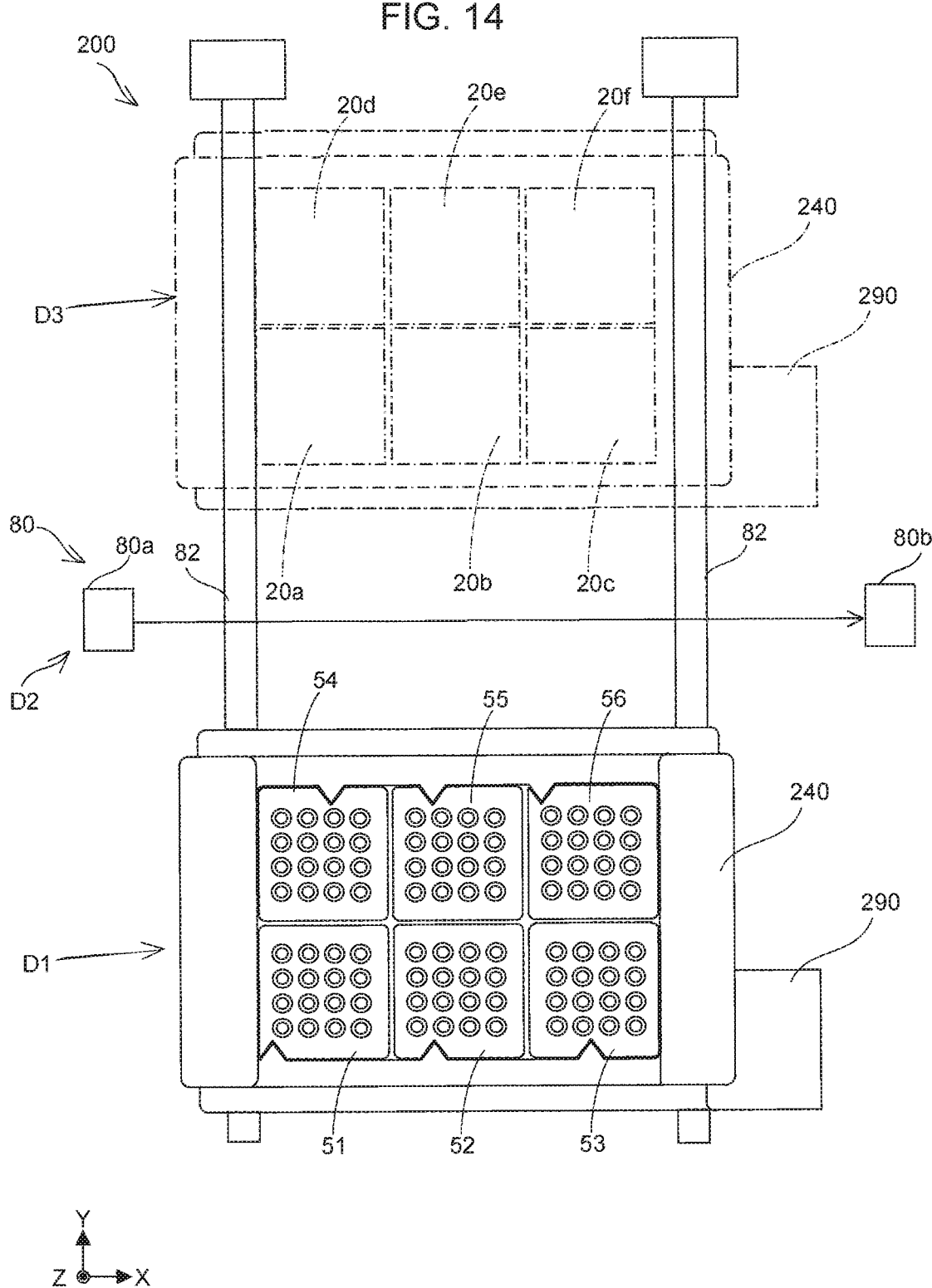

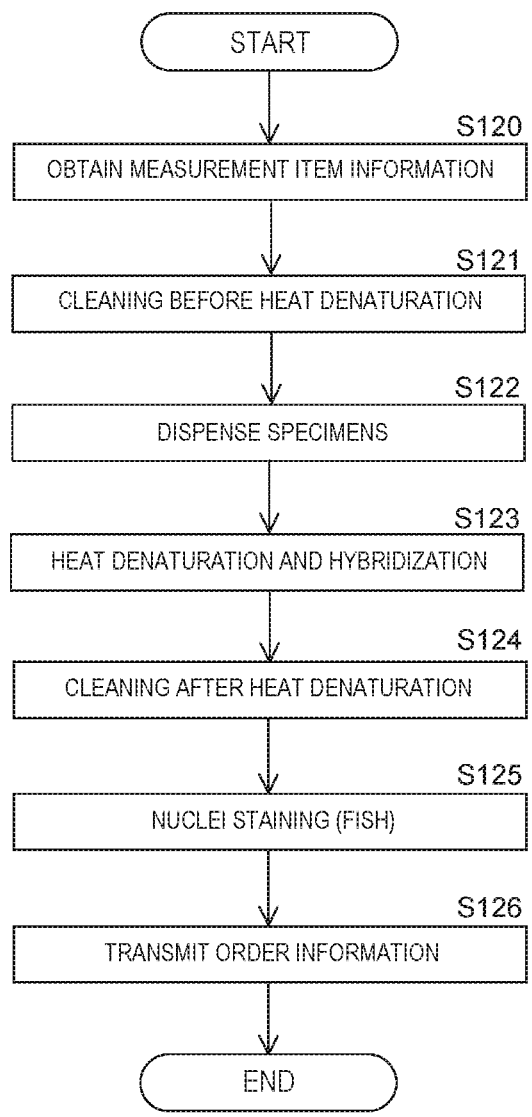

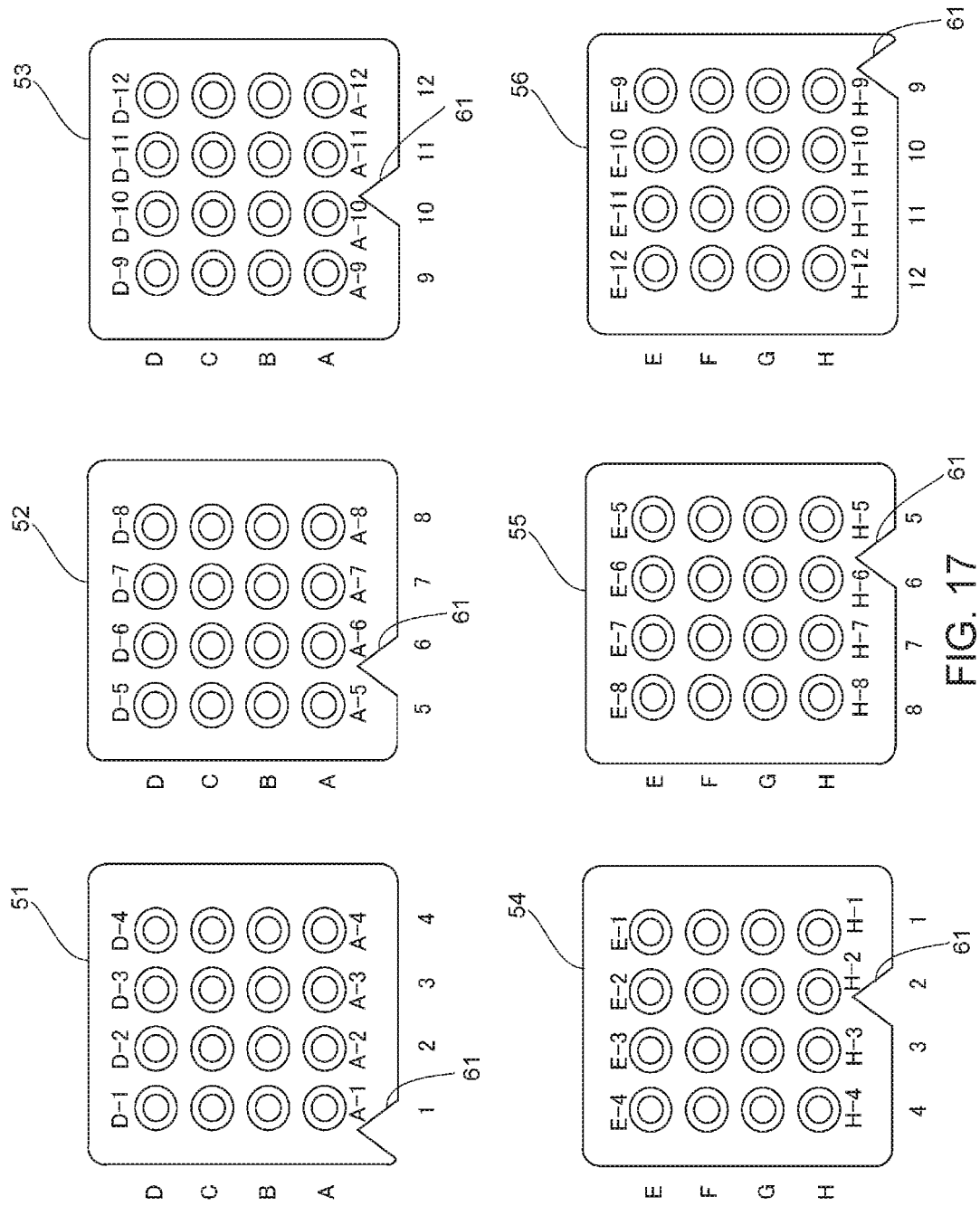

FIG. 18

| POSITION INFORMATION | SAMPLE ID | MEASUREMENT ITEM |
|---|---|---|
| A-1 | 0001 | BCR-ABL |
| A-2 | 0002 | IGH/FGFR3 |
| A-3 | 0003 | IGH/MAF |
| D-4 | 0016 | CKS1b |
| A-5 | 0017 | PML-RARα |
| A-6 | 0018 | EVI1 |
| A-7 | 0019 | D13S319 |
| D-8 | 0032 | P53 (TP53) Deletion |

| POSITION INFORMATION | SAMPLE ID | MEASUREMENT ITEM | MEASUREMENT ANALYSIS RESULT |
|---|---|---|---|
| A-1 | 0001 | BCR-ABL | ... |
| A-2 | 0002 | IGH/FGFR3 | ... |
| A-3 | 0003 | IGH/MAF | ... |
| D-4 | 0016 | CKS1b | ... |
| A-5 | 0017 | PML-RARα | ... |
| A-6 | 0018 | EVI1 | ... |
| A-7 | 0019 | D13S319 | ... |
| D-8 | 0032 | P53 (TP53) Deletion | ... |
| A-9 | 0033 | IGH/FGFR3 | ... |
| A-10 | 0034 | EVI1 | ... |
| A-11 | 0035 | CKS1b | ... |
| D-12 | 0048 | PML-RARα | ... |
| E-1 | 0049 | P53 (TP53) Deletion | ... |
| E-2 | 0050 | EVI1 | ... |
| E-3 | 0051 | BCR-ABL | ... |
| H-4 | 0064 | CKS1b | ... |
| E-5 | 0065 | BCR-ABL | ... |
| E-6 | 0066 | PML-RARα | ... |
| E-7 | 0067 | D13S319 | ... |
| H-8 | 0080 | P53 (TP53) Deletion | ... |
| E-9 | 0081 | PML-RARα | ... |
| E-10 | 0082 | IGH/FGFR3 | ... |
| E-11 | 0083 | D13S319 | ... |
| H-12 | 0096 | P53 (TP53) Deletion | ... |

FIG. 20

SPECIMEN PROCESSING APPARATUS, SPECIMEN MEASUREMENT SYSTEM AND METHOD FOR PROCESSING SPECIMEN

CROSS REFERENCE TO RELATED APPLICATIONS

This application claims priority from to prior Japanese Patent Application No. 2019-153282 filed with the Japan Patent Office on Aug. 23, 2019, the entire contents of which are incorporated herein by reference.

BACKGROUND

The disclosure relates to a specimen processing apparatus, a holder, a specimen measurement system and a method for processing a specimen.

There are known specimen processing apparatuses that perform processing such as centrifugation, decapping, and specimen dispensing on specimens such as blood and urine or containers containing those specimens. As such a specimen processing apparatus, for example, a sample test automation system disclosed in International Patent Publication No. WO2011-148897 ("Patent Literature 1") includes a sample input unit having tray storage units that each house a sample tray holding samples and a specimen processing unit including a centrifugal unit, a decapping unit, and a dispensing unit. This sample test automation system switches the method of the specimen processing unit processing samples, based on identifiers attached to the sample trays held in the tray storage unit, the positions of the held sample trays, or the compartment positions of the sample trays.

The sample test automation system disclosed in patent literature 1 needs to have an identifier reading apparatus, in the case of switching the method of processing samples based on the identifiers attached to the sample trays. This makes the apparatus structure complicated. In the case of switching the method of processing samples based on the positions of the held sample trays or the compartment positions of the sample trays, the sample test automation system does not need an identifier reading apparatus. However, if the operator places sample trays at wrong positions, the samples are processed by a method different from the one desired by the operator.

One or more aspects have been made in light of the above situation, and an object thereof is to provide a specimen processing apparatus, a holder, and a specimen measurement system that make it possible to process specimens by the method desired by the operator without complicating the structure.

SUMMARY

A specimen processing apparatus according to one or more aspects performs processing on a specimen contained in a container. The specimen processing apparatus includes: holders having different shapes, each of the holders being configured to hold the container; a holder placement unit that comprises holder receiving portions having different shapes, the shapes of the holder receiving portions corresponding to the shapes of the holders; and a specimen processing unit that performs processing on the specimen contained in the container held by one of the holders placed on the holder placement unit.

A specimen measurement system according to one or more aspects includes: a specimen preparation apparatus that prepares a specimen using a reagent; and a measurement apparatus that measures a specimen prepared by the specimen preparation apparatus, wherein the specimen preparation apparatus prepares the specimen in a container, and the measurement apparatus comprises: holders having different shapes, each of the holders being configured to hold the container; a holder placement unit that comprises holder receiving portions having different shapes, the shapes of the holder receiving portions corresponding to the shapes of the holders; and a specimen processing unit that performs processing on the specimen contained in the container held by one of the holders placed on the holder placement unit.

A method for processing a specimen according to one or more aspects includes: placing first and second holders having different shapes and each formed to hold at least one container, on holder receiving portions of a specimen measurement apparatus, the shapes of the holder receiving portions being different from one another and corresponding to the shapes of the holders; dispensing, by the specimen measurement apparatus, a specimen in the at least one container on the holder held by the holder receiving portions; and processing, by the specimen measurement apparatus, the specimen in the containers held by the holders.

BRIEF DESCRIPTION OF DRAWINGS

FIGS. 5A, 5B, and 5C are schematic diagrams each illustrating a placement unit included in a specimen preparation apparatus according to an embodiment and holders which are placed on a placement unit;

FIG. 7 is a block diagram illustrating a schematic configuration of a control unit of a specimen preparation apparatus according to an embodiment;

FIG. 14 is a schematic diagram illustrating a state in which a placement unit and holders according to an embodiment are attached to a support unit of a measurement apparatus and being transferred;

FIG. 16 is a flow diagram illustrating processing performed by a controller of a specimen preparation apparatus according to an embodiment;

FIG. 17 is a schematic diagram illustrating position information on specimens in holders according to an embodiment;

FIG. 18 is a diagram illustrating order information stored in a memory of a specimen preparation apparatus according to an embodiment;

FIG. 20 is a diagram illustrating order information stored in a memory of a measurement apparatus according to an embodiment.

DETAILED DESCRIPTION

Figure 1:
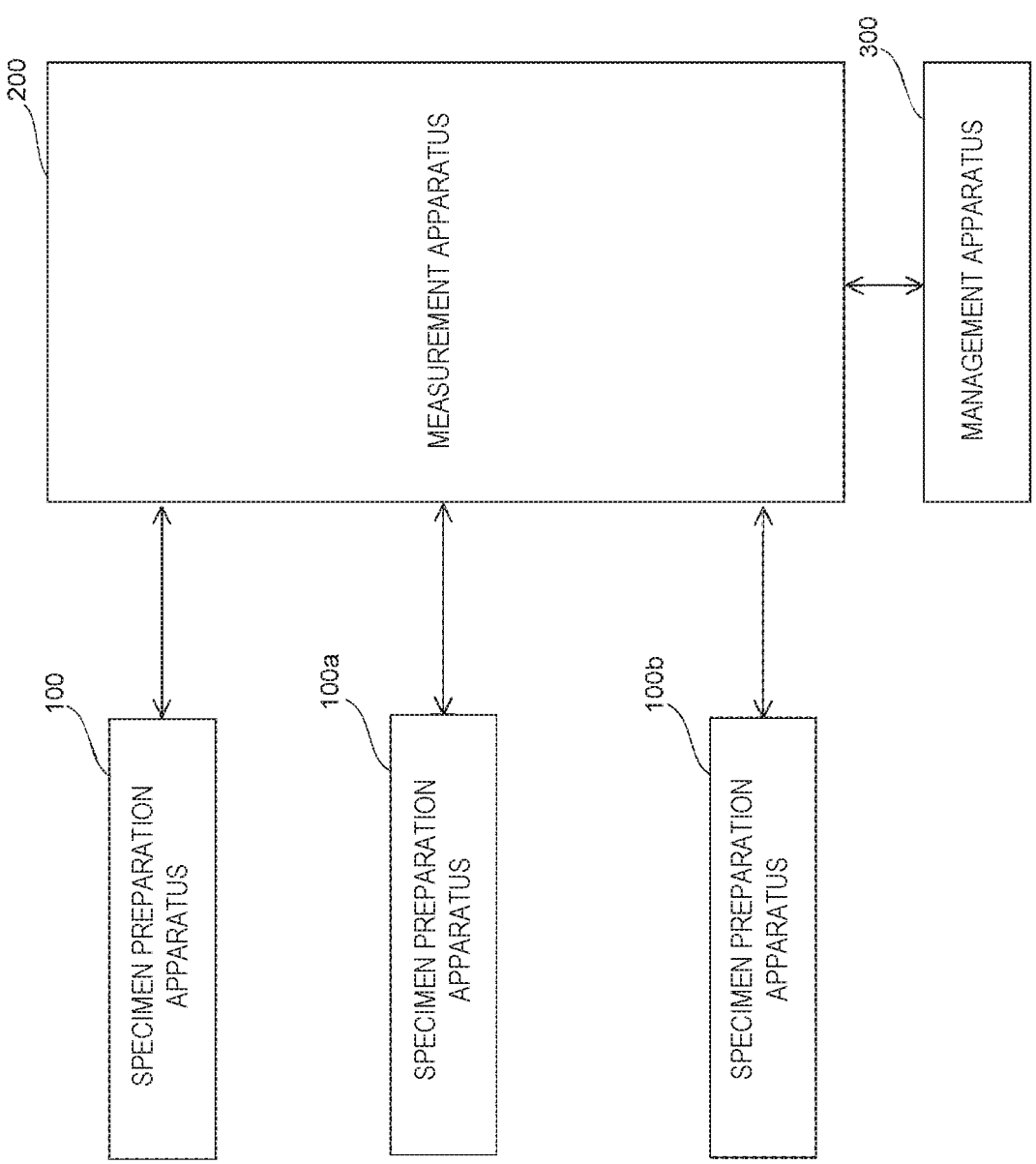
FIG. 1 is a schematic diagram illustrating a specimen measurement system according to an embodiment.

A specimen processing apparatus (100, 100a, 100b, 200) according to one or more aspects performs processing on a specimen contained in a container. The specimen processing apparatus includes: holders (51 to 56) that are formed in shapes different from one, each of the holders being configured to hold the container; a holder placement unit (140, 240) including holder receiving portions (120a to 120f) that are formed in shapes different from one another and each fit the shape of a different one of the holders; and a specimen processing unit (105, 280) that performs processing on the specimen contained in the container held by the holder placed on the holder placement unit.

A specimen measurement system according to one or more aspects includes: a specimen preparation apparatus (100, 100a, 100b) that prepares a specimen using a reagent; and a measurement apparatus (200) that measures a specimen prepared by the specimen preparation apparatus. The specimen preparation apparatus prepares the specimen in a container. The measurement apparatus includes holders (51 to 56) that are formed in shapes different from one another, each of the holders being configured to hold the container, a holder placement unit (240) including holder receiving portions that are formed in shapes different from one another and each fit the shape of a different one of the holders, and a specimen processing unit (105, 280) that performs processing on the specimen contained in the container held by the holder placed on the holder placement unit.

One or more aspects provide a specimen processing apparatus, a holder, and a specimen measurement system that make it possible to process specimens by the method desired by the operator without complicating the structure.

<Specimen Measurement System>

Hereinafter, a specimen measurement system according to an embodiment is described by taking an example of detecting test substances (genes) included in blood samples using fluorescence in situ hybridization (FISH).

A specimen measurement system 1 illustrated in FIG. 1 is installed at a facility such as a hospital or a laboratory. The specimen measurement system 1 determines test substances (genes) as measurement items based on order information issued for blood samples and performs pretreatments necessary for detecting the test substances (genes) and measurement analyses. This specimen measurement system 1 includes specimen preparation apparatuses 100, 100a, and 100b, a measurement apparatus 200, and a management apparatus 300. Each of the specimen preparation apparatuses 100, 100a, and 100b is for performing pretreatments on blood samples including test substances, such as adding fluorescent labeling reagents and heating, and prepares specimens for each measurement item based on order information issued for each blood sample. The measurement apparatus 200 performs optical measurement and analysis on specimens prepared by the specimen preparation apparatuses 100, 100a, and 100b. The management apparatus 300 is a computer that manages order information on blood samples. The management apparatus 300, the measurement apparatus 200, and the specimen preparation apparatuses 100, 100a, and 100b are connected to communicate order information. Although in an embodiment, the management apparatus 300 and the measurement apparatus 200 are connected via an in-house LAN, and the measurement apparatus 200 and the specimen preparation apparatuses 100, 100a, and 100b are connected in a peer-to-peer manner, the present disclosure is not limited to this configuration. The order information is a set of information including identification information for identifying blood samples and measurement items for blood samples.

The measurement apparatus 200 performs measurement and analysis sequentially on a large number of specimens prepared by the three specimen preparation apparatuses 100, 100a, and 100b. Usually, the processing in the specimen preparation apparatuses needs takes a relatively long time, 10 to 24 hours, whereas the processing in the measurement apparatus finishes in a relatively short time, which is about several hours. For this reason, multiple specimen preparation apparatuses are operated to process a large number of specimens in parallel to improve the operating ratio of the measurement apparatus and perform measurement analysis efficiently on specimens.

<Procedure for Specimen Preparation and Measurement Using Specimen Measurement System>

Figure 2:
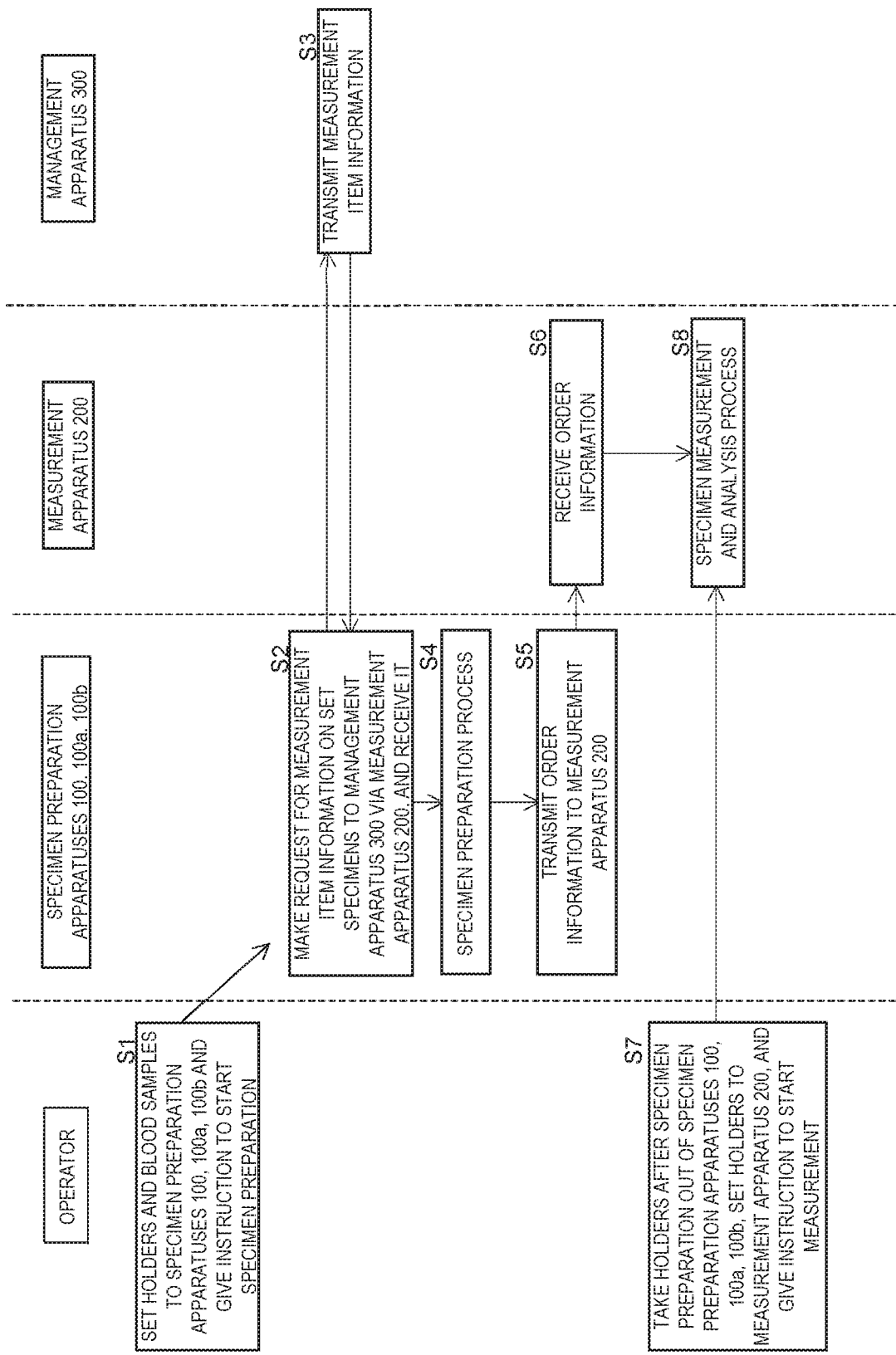
FIG. 2 is a diagram illustrating procedure of specimen preparation and measurement by a specimen measurement system according to an embodiment.

At step S1 illustrated in FIG. 2, the operator places holders holding empty containers and blood samples for measurement on a holder placement unit in each of the specimen preparation apparatuses 100, 100a, and 100b and gives an instruction to start preparing specimens to each of the specimen preparation apparatuses 100, 100a, and 100b. Receiving the start instruction, each of the specimen preparation apparatuses 100, 100a, and 100b, at step S2, makes a request for the measurement items for the placed blood samples to the management apparatus 300 via the measurement apparatus 200 and then receives the measurement items. In response to the request, the management apparatus 300, at step S3, transmits the measurement items to each of the specimen preparation apparatuses 100, 100a, and 100b via the measurement apparatus 200. At step S4, each of the specimen preparation apparatuses 100, 100a, and 100b, based on the received measurement items, prepares blood samples in the containers held by the holders placed by the operator. At step S5, each of the specimen preparation apparatuses 100, 100a, and 100b transmits order information including the measurement items received at step S2, to the measurement apparatus 200. At step S6, the measurement apparatus 200 received the order information from each of the specimen preparation apparatuses 100, 100a, and 100b.

At step S7, the operator takes the containers containing blood samples after preparation out of each of the specimen preparation apparatuses 100, 100a, and 100b, places the containers on a holder placement unit of the measurement apparatus 200, and gives an instruction to start measurement to the measurement apparatus 200. At step S8, the measurement apparatus 200 performs measurement and analysis on the blood samples after preparation placed by the operator, based on the received order information.

<Specimen Preparation Apparatus>

The specimen preparation apparatuses 100, 100a, and 100b have the same or similar configurations, and hence, the specimen preparation apparatus 100 is described as an example.

Figure 3:
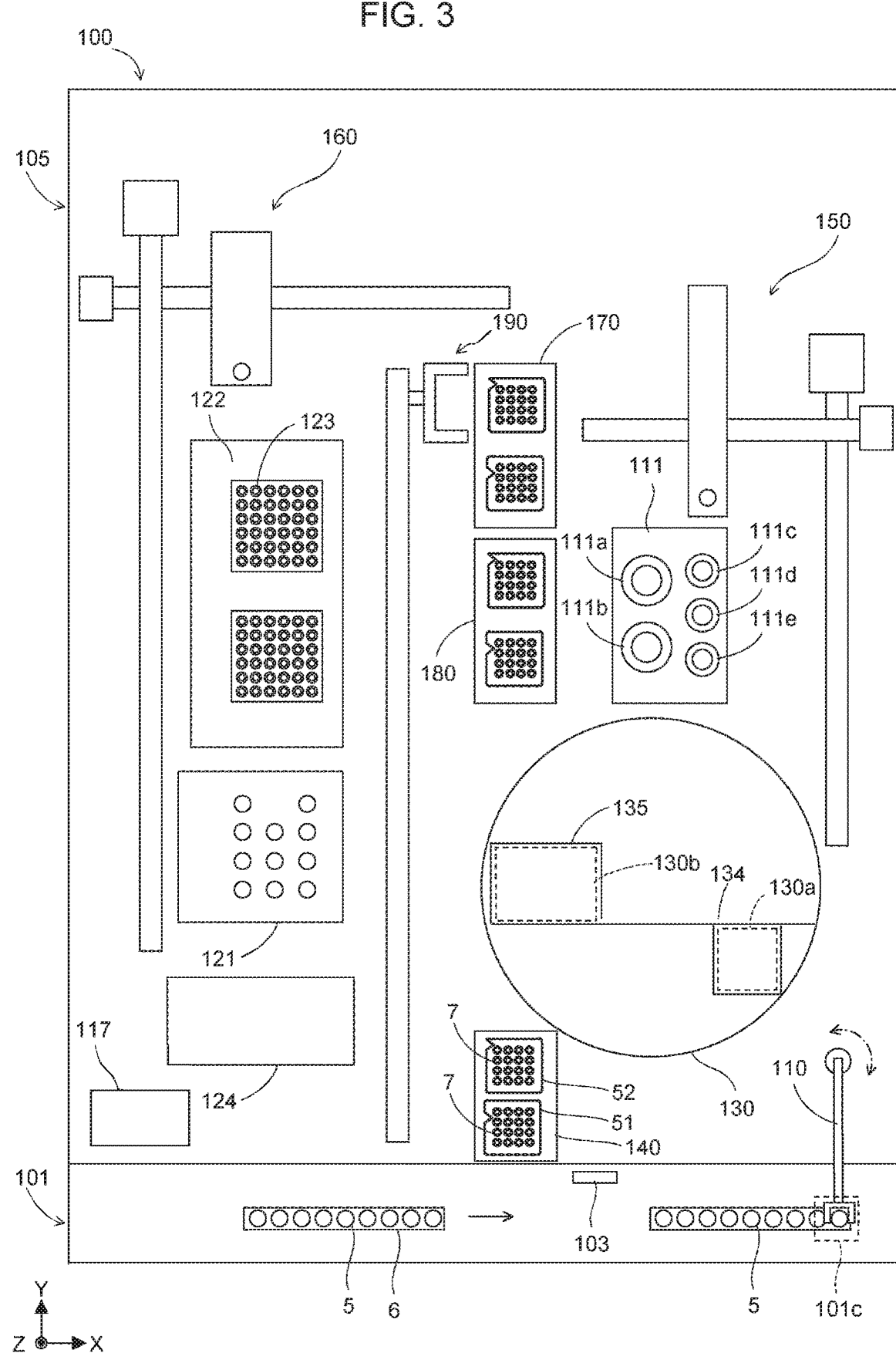
FIG. 3 is a schematic plan view diagram illustrating a specimen preparation apparatus according to an embodiment.

As illustrated in FIG. 3, the specimen preparation apparatus 100 includes a rack transporter 101 and a specimen preparation unit 105. The rack transporter 101 transports racks 6 holding specimen containers 5 containing blood samples along the X-axis direction.

Figure 4:
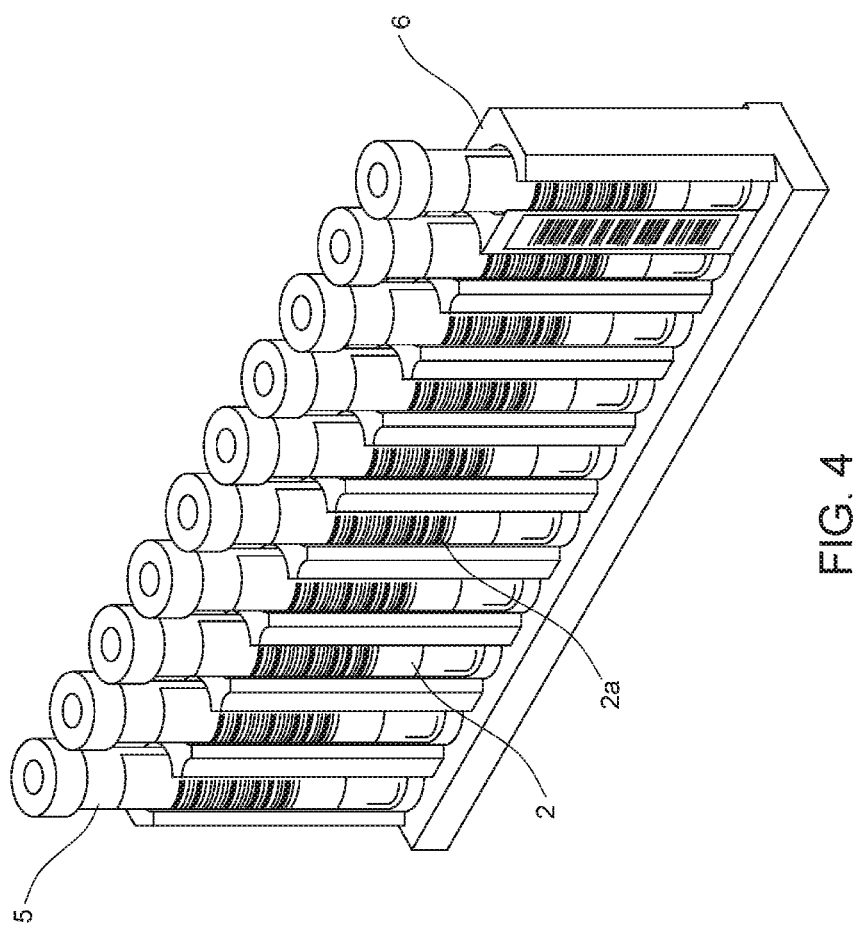
FIG. 4 is a diagram illustrating a rack which is supplied to a specimen preparation apparatus according to an embodiment.

As illustrated in FIG. 4, the specimen containers 5 held in the rack 6 has a barcode label 2 attached on it. The barcode label 2 has a printed barcode 2a including information on a sample ID given to each specimen container 5.

Returning to FIG. 3, the rack transporter 101 includes a barcode reader 103, which reads the sample ID from the barcode 2a of the barcode label 2 attached to the specimen container passing in front of the barcode reader 103.

The specimen preparation unit 105 includes a receiving mechanism 110, first reagent setting unit 111, second reagent setting unit 121, chip setting unit 122, discarding unit 124, centrifugal reaction unit 130, first dispensing mechanism 150, second dispensing mechanism 160, first heater unit 170, second heater unit 180, transportation mechanism 190, placement unit 140, and control unit 117.

The receiving mechanism 110 takes the specimen container 5 positioned at a reception position 101c on the rack transporter 101 out of the rack 6 and sets the specimen container 5 to the centrifugal reaction unit 130. The transportation mechanism 190 is a mechanism to hold and transport holders 51 and 52, which transports the holders 51 and 52 to the placement unit 140, centrifugal reaction unit 130, first heater unit 170, and second heater unit 180.

The first dispensing mechanism 150 sucks in reagents from reagent containers 111a to 111e set on a first reagent setting unit 111 and discharges the reagents into containers positioned on the centrifugal reaction unit 130. The second dispensing mechanism 160 sucks in reagents from the reagent containers set in the second reagent setting unit 121 and discharges the reagents into containers positioned on the centrifugal reaction unit 130. The second dispensing mechanism 160 is capable of equipping itself with disposable chips and taking off them. The disposal chips are discarded after each suction and discharge of reagents. The second dispensing mechanism 160 equips itself with chips 123 placed on the chip setting unit 122, sucks in and discharges reagents, and then discards the chips 123 to the discarding unit 124.

The first reagent setting unit 111 is configured to accommodate five reagent containers 111a to 111e. The reagent containers 111a and 111b contain a 0.5% BSA-in-PBS solution. The reagent containers 111c, 111d, and 111e contain 0.4×SSC, 2×SSc, and DRAQS, respectively.

The second reagent setting unit 121 is configured to accommodate reagent containers containing reagents for FISH. The chip setting unit 122 is configured to accommodate multiple disposable chips 123. The discarding unit 124 collects chips 123 that have been used and are to be discarded.

The centrifugal reaction unit 130 is capable of rotating horizontally and used for centrifuging blood samples. The centrifugal reaction unit 130 has, on its upper surface, openings 130a and 130b and shutters 134 and 135 for opening and closing the openings 130a and 130b. The shutters 134 and 135 are controlled to open when the centrifugal reaction unit 130 is accessed from the outside via the openings 130a and 130b and be closed in the other time.

The first heater unit 170 and the second heater unit 180 hold the holders 51 and 52 transported by the transportation mechanism 190 and are configured to heat the reagents and the specimens contained in the holders 51 and 52 to a specified temperature higher than room temperature.

The placement unit 140 is located at a position where the operator can access and configured to receive two holders 51 and 52.

As illustrated in FIG. 7, the control unit 117 includes a controller 107, a memory 109, a communication unit 113, and an input-output unit 112. The communication unit 113 includes a first interface 114. The controller 107 includes a CPU and executes programs stored in the memory 109 to control each unit of the specimen preparation apparatus 100. The memory 109 includes ROM, RAM, and a hard disk. The input-output unit 112 includes a touch panel display and is configured to receive various operations including the instruction to start the specimen preparation apparatus 100 by the operator and display a screen indicating the state of the specimen preparation apparatus 100 and a screen for receiving operation input from the operator. The communication unit 113 receives information from the measurement apparatus 200 and transmits information to the measurement apparatus 200 via the first interface 114 for connecting to the measurement apparatus 200.

The placement unit 140, as illustrated in FIG. 5A, has a shape that fits specific holders and includes adapters 120a and 120b in recessed shapes for receiving the holders. The adapter 120a has a shape that fits the holder 51, and the adapter 120b has a shape that fits the holder 52.

The holders 51 and 52 have engagement portions 61. The adapters 120a and 120b have engagement portions 62. The engagement portion 61 of the holder 51 and the engagement portion 62 of the adapter 120a are formed at positions where those are engaged with each other. The engagement portion 61 of the holder 52 and the engagement portion 62 of the adapter 120b are also formed at positions where those are engaged with each other. The shapes of the engagement portions 61 of the holder 51 and the holder 52 are the same, but the positions of those on the holder side surfaces in the width directions are different from each other. Similarly, the shapes of the engagement portions 62 of the adapter 120a and the adapter 120b are the same, but the positions of those on the inner side surfaces of the adapters in the width direction are different from each other.

Figure 6C:
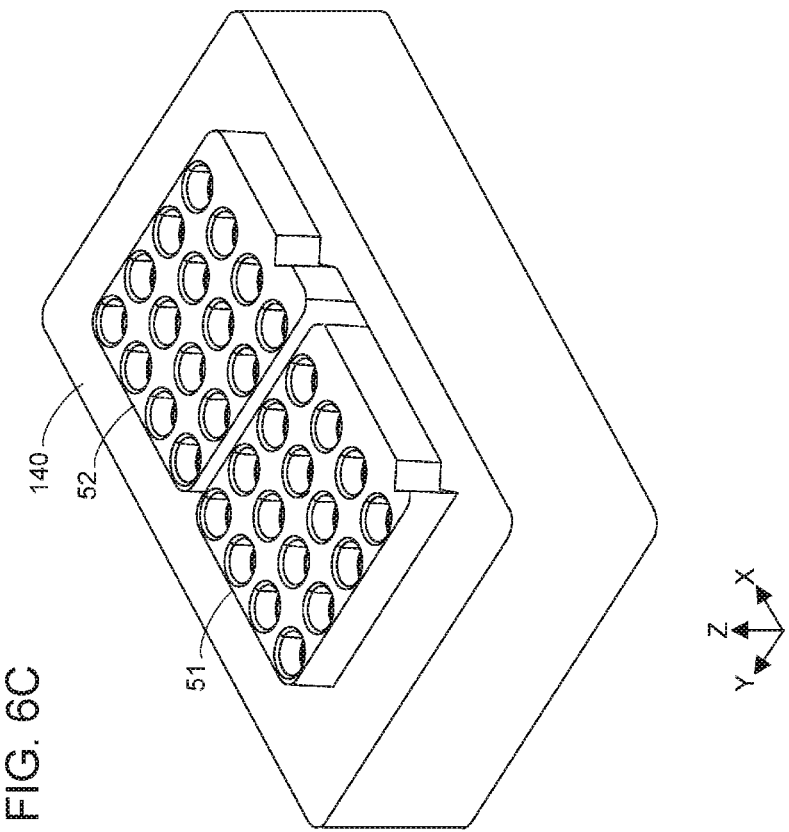
FIGS. 6A, 6B, and 6C are perspective views illustrating holders according to an embodiment.

As illustrated in FIG. 6C, the holders 51 and 52 are formed such that the upper surfaces of the holders 51 and 52 are higher than the upper surfaces of the placement unit 140 around the holders in the state where the holders 51 and 52 are placed in the placement unit 140. This configuration allows the transportation mechanism 190 to hold the holders 51 and 52 and also allows the operator to attach or detach the holders 51 and 52 easily to the placement unit 140.

The placement unit 140a of the specimen preparation apparatus 100a and the placement unit 140b of the specimen preparation apparatus 100b are illustrated in FIGS. 5B and 5C, respectively. The placement unit 140a, as illustrated in FIG. 5B, has a shape that fits specific holders and includes adapters 120c and 120d in recessed shapes for receiving the holders. The adapter 120c has a shape that fits a holder 53, and the adapter 120d has a shape that fits a holder 54. The placement unit 140b, as illustrated in FIG. 5C, has a shape that fits specific holders and includes adapters 120e and 120f in recessed shapes for receiving the holders. The adapter 120e has a shape that fits a holder 55, and the adapter 120f has a shape that fits a holder 56. In the holders 51 to 56, the shapes of the engagement portions 61 are the same, but the positions of those on the holder side surfaces in the width directions are different from one another. In the adapters 120a to 120f, the shapes of the engagement portions 62 are the same, but the positions of those on the inner side surfaces of the adapters in the width directions are different from one another.

Figure 6A:
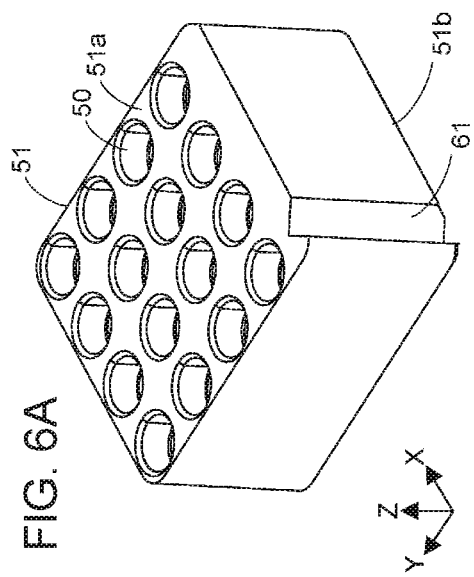
Figure 6B:
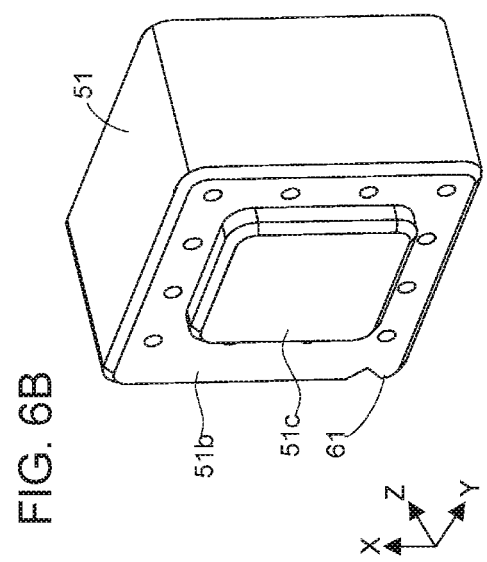

Here, the shapes of the holders 51 to 56 are described by taking the holder 51 as an example. As illustrated in FIGS. 6A and 6B, the holder 51 has a rectangular parallelepiped shape, and the upper surface 51a of the holder 51 has holding portions 50 for holding containers containing specimens, which are arranged in four lines and four rows, and the total number of which is 16. One side surface of the holder 51 has an engagement portion 61 which is a recess in the shape of a ditch extending from the bottom surface 51b to the upper surface 51a. The bottom surface 51b of the holder 51 has a protruding portion 51c in a rectangular shape in a plan view. The holders 52 to 56 have the same shape as the holder 51 except that the positions of the engagement portions 61 on the holder side surfaces in the width directions are different.

The configurations of the holders 51 to 56 and the adapters 120a to 120f as described above allow the holders 51 to 56 to be placed in the adapters 120a to 120f in only specified orientations.

<Measurement Apparatus>

Figure 8:
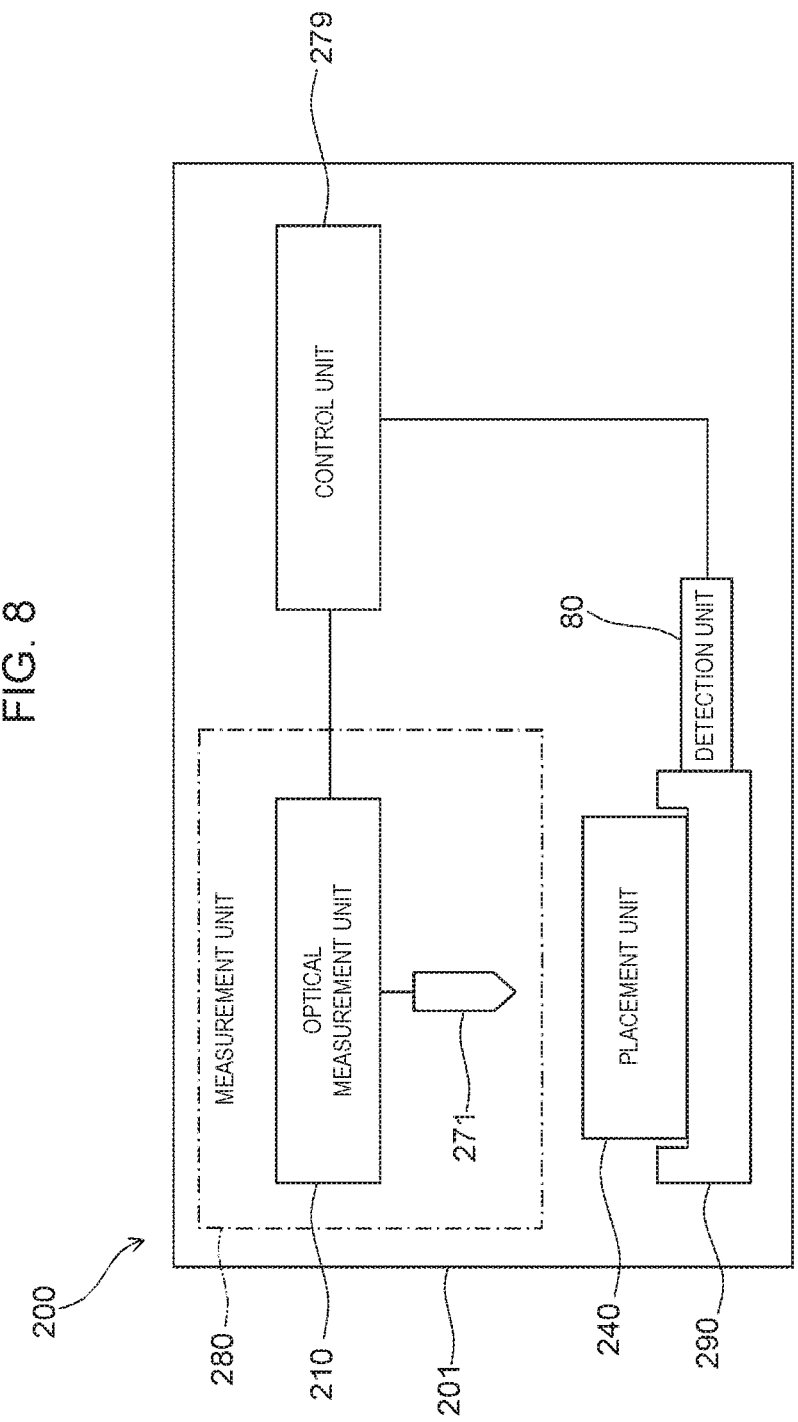
FIG. 8 is a schematic diagram illustrating a measurement apparatus according to an embodiment.

The measurement apparatus 200, as illustrated in FIG. 8, includes a measurement unit 280, a control unit 279 that controls the operation of the measurement unit 280, a placement unit 240, a support unit 290 that attachably and detachably supports the placement unit 240, and a detection unit 80. Those units are housed in a box-shaped part 201.

On the placement unit 240 are placed the holders 51 to 56 holding containers containing blood samples prepared in the specimen preparation apparatuses 100, 100a, and 100b.

The measurement unit 280 includes an optical measurement unit 210 for performing optical measurement on specimens and a suction unit 271 that sucks in a blood sample placed on the placement unit 240 and supplies the sucked blood sample to the optical measurement unit 210.

Figure 9:
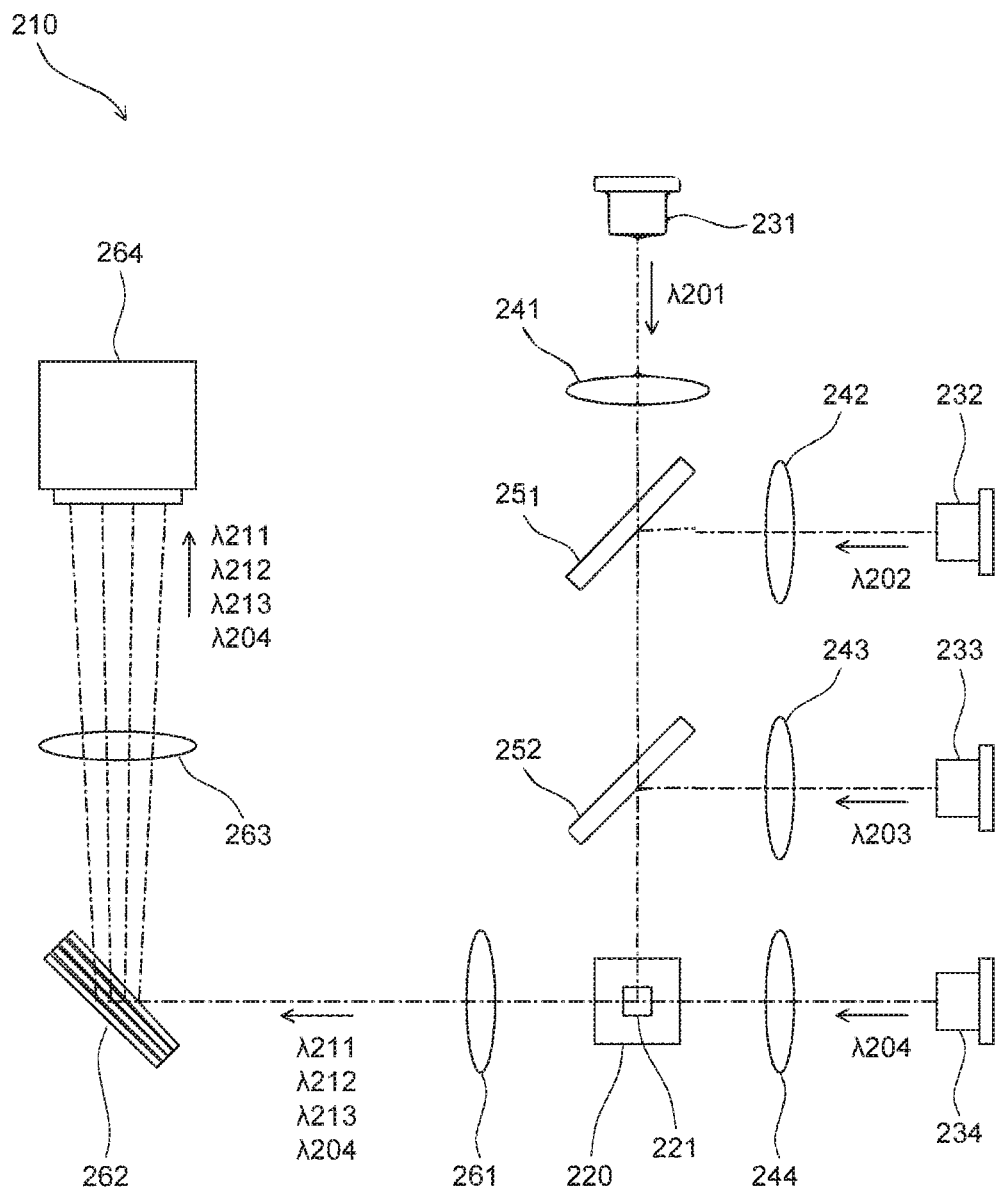
FIG. 9 is a schematic diagram illustrating a schematic configuration for explaining an optical measurement unit of a measurement apparatus according to an embodiment.

The optical measurement unit 210, as illustrated in FIG. 9, includes a flow cell 220, light sources 231 to 234, condenser lenses 241 to 244, dichroic mirrors 251 and 252, a condenser lens 261, an optical unit 262, a condenser lens 263, and an imaging unit 264. Specimens flow through the flow path 221 of the flow cell 220.

The light sources 231 to 234 irradiates the specimens flowing through the flow cell 220 with light. The light sources 231 to 234 each include a semiconductor laser light source. The light beams emitted from the light sources 231 to 234 are laser light beams having wavelengths of λ201 to λ204, respectively. The condenser lenses 241 to 244 collect light emitted from the light sources 231 to 234, respectively. The dichroic mirror 251 allows light having a wavelength of λ201 to pass and reflects light having a wavelength of λ202. The dichroic mirror 252 allows light having wavelengths of λ201 and λ202 and reflects light having a wavelength of λ203. Thus, light having wavelengths of λ201 to λ203 is projected via the dichroic mirror 252 to the specimens flowing through the flow path 221 of the flow cell 220. Light having a wavelength of λ204 is projected via the condenser lens 244 to the specimens flowing through the flow path 221 of the flow cell 220.

When the specimens flowing through the flow cell 220 are irradiated with light having a wavelength of λ201, a fluorescent dye used for staining cells generates fluorescence having a wavelength of λ211. When the specimens flowing through the flow cell 220 are irradiated with light having a wavelength of λ202, a fluorescent dye used for staining cells generates fluorescence having a wavelength of λ212. When the specimens flowing through the flow cell 220 are irradiated with light having a wavelength of λ203, a fluorescent dye used for staining cells generates fluorescence having a wavelength of λ213. When the specimens flowing through the flow cell 220 are irradiated with light having a wavelength of λ204, the light passes through the cells. The light having a wavelength of λ204 passed through the cells is used to generate a bright field image.

The condenser lens 261 collects fluorescence having wavelengths of λ211 to λ213 generated from the specimens flowing through the flow path 221 of the flow cell 220 and light having a wavelength of λ204 that has passed through the specimens flowing through the flow path 221 of the flow cell 220. The optical unit 262 has, for example, a configuration including a combination of four dichroic mirrors or a prism. The optical unit 262 reflects fluorescence having wavelengths of λ211 to λ213 and light having a wavelength of λ204 at angles slightly different from one another and separates them on the light receiving surface of the imaging unit 264. The condenser lens 263 collects fluorescence having wavelengths of λ211 to λ213 and light having a wavelength of λ204.

The imaging unit 264 includes, for example, a time-delay-integration (TDI) camera. The imaging unit 264 captures images of fluorescence having wavelengths of λ211 to λ213 and light having a wavelength of λ204 and outputs fluorescence images respectively corresponding to fluorescence having wavelengths of λ211 to λ213 and a bright field image corresponding to light having a wavelength of λ204 as image signals.

Figure 10:
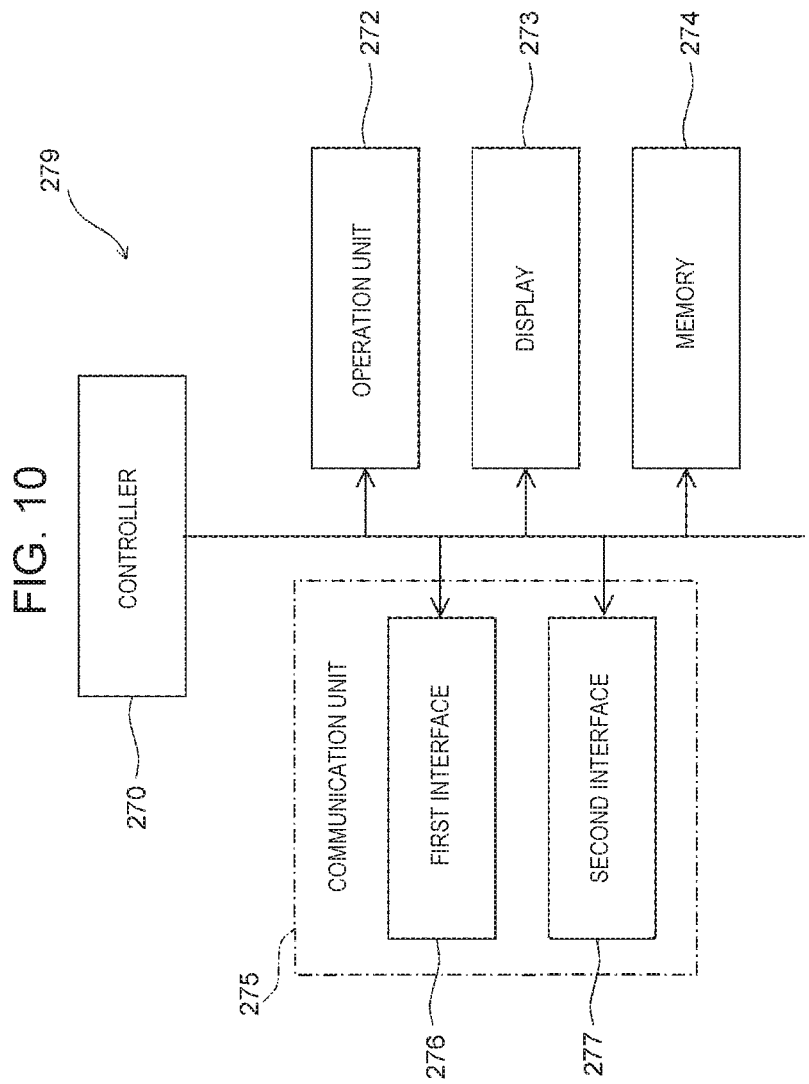
FIG. 10 is a block diagram illustrating a schematic configuration a control unit of a measurement apparatus according to an embodiment.

The control unit 279, as illustrated in FIG. 10, includes a controller 270, operation unit 272, display 273, memory 274, and communication unit 275. The controller 270 includes a CPU and executes programs stored in the memory 274 to control each unit of the measurement apparatus 200. The memory 274 includes ROM, RAM, and a hard disk. The operation unit 272 includes a mouse and a keyboard and is configured to receive various operations including the instruction to start the measurement apparatus 200 by the operator. The display 273 displays a screen indicating the state of the measurement apparatus 200 and a screen for receiving operation input by the operator. The communication unit 275 includes a first interface 276 for connecting to the specimen preparation apparatuses 100, 100a, and 100b and a second interface 277 for connecting to the management apparatus 300 and transmits and receives information.

Figure 11:
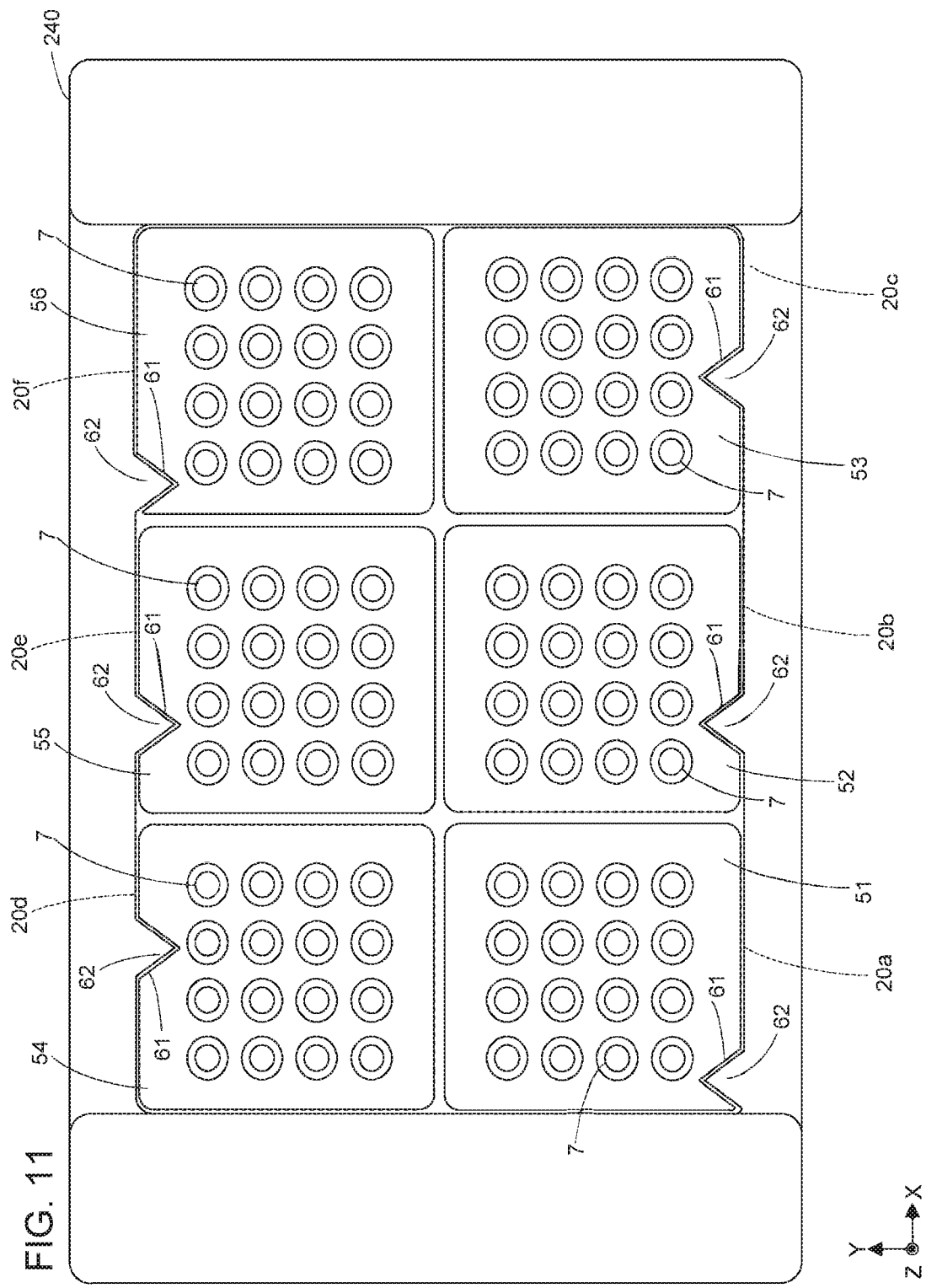
FIG. 11 is a schematic diagram illustrating a placement unit included in a measurement apparatus according to an embodiment and holders placed on a placement unit.
Figure 12:
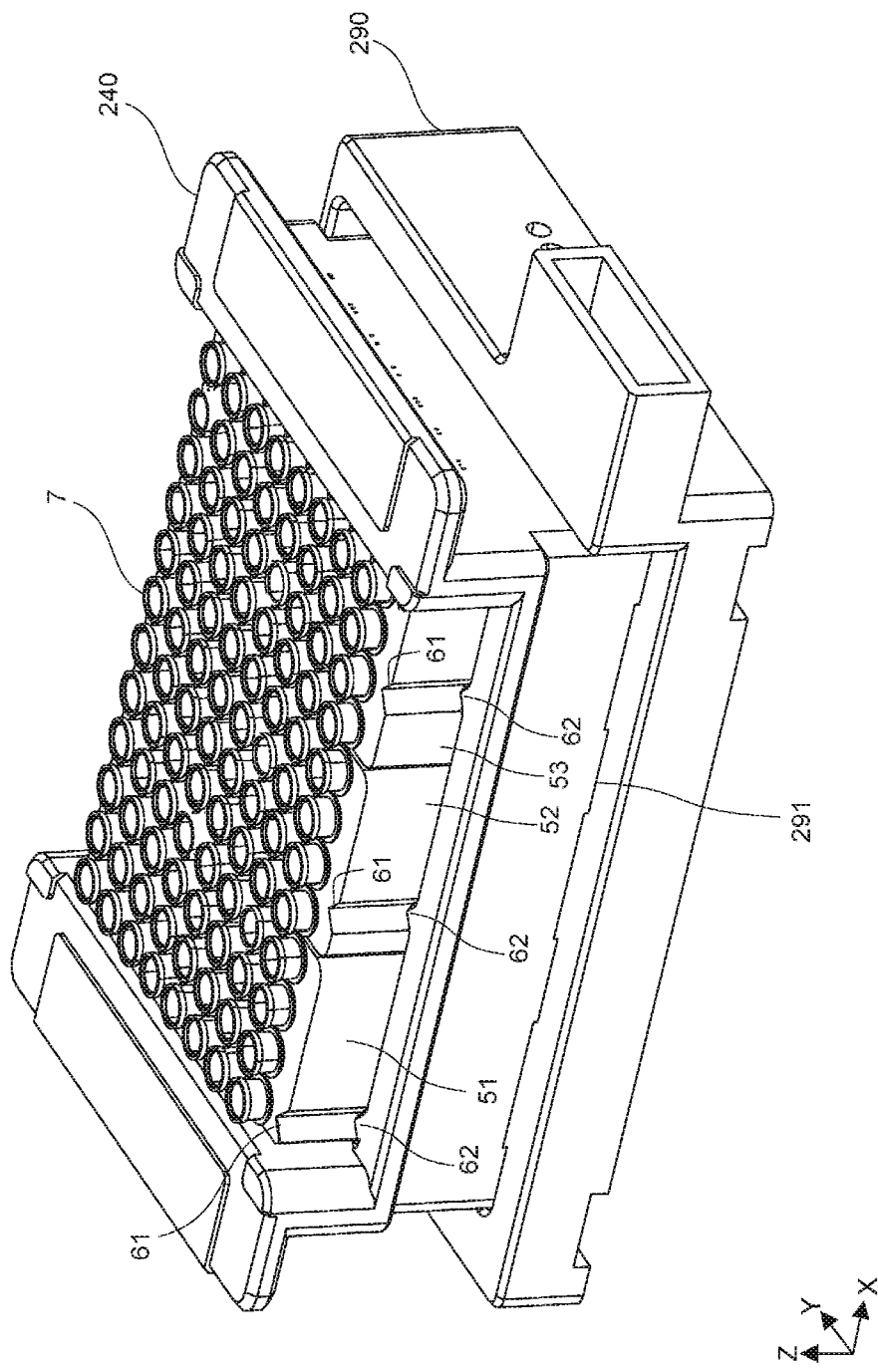
FIG. 12 is a perspective view illustrating a support unit included in a measurement apparatus according to an embodiment on which a placement unit and holders are attached.
Figure 13:
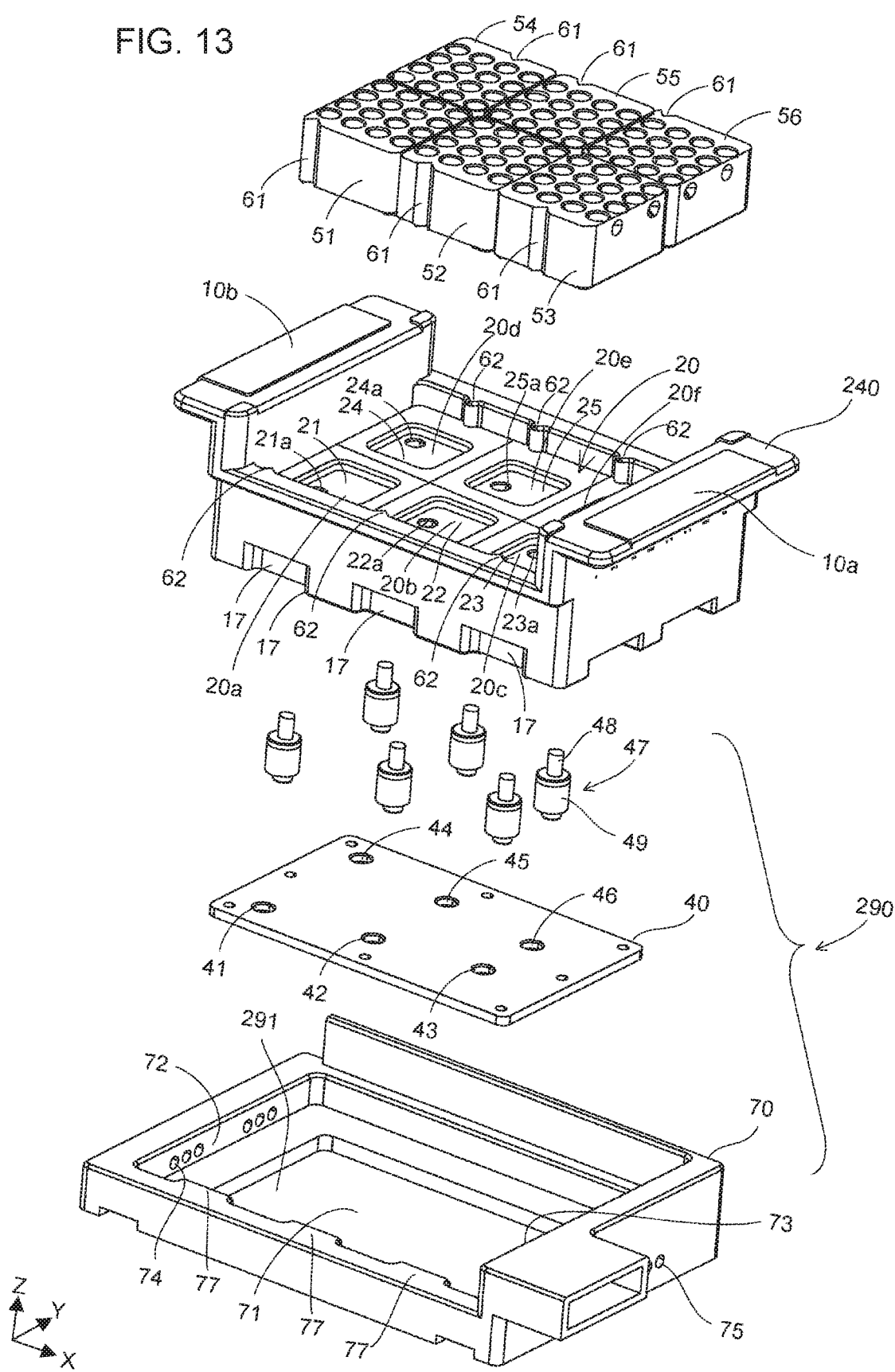
FIG. 13 is an exploded perspective view illustrating a support unit included in a measurement apparatus according to an embodiment and perspective views illustrating a placement unit and holders.

As illustrated in FIGS. 11 to 13, the placement unit 240 includes adapters 20a, 20b, 20c, 20d, 20e, and 20f that respectively receive the holders 51 to 56. The six adapters 20a to 20f have shapes that respectively fit the six holders 51 to 56, and each include an engagement portion 62. In the six adapters 20a to 20f, the shapes of the engagement portions 62 are the same, but the positions of those on the inner side surfaces of the adapters in the width directions are different from one another. The six holders 51 to 56 are placed to adjoin one another in a recess the bottom surface of which is the inner bottom surface 20 of the placement unit 240. In this process, each engagement portion 61 and the respective engagement portion 62 are engaged, the holders 51 to 56 are positioned within the recess of the placement unit 240. As illustrated in FIG. 12, the holders 51 to 56 protrude upward from the recess of the placement unit 240. This allows the operator to attach and detach the holders 51 to 56 easily to and from the recess of the placement unit 240.

As illustrated in FIG. 13, the inner bottom surface 20 of the placement unit 240 has six recesses 21 to 26. Into the six recesses 21 to 26 are fitted the protruding portions (the protruding portions 51c in FIG. 6) formed on the bottom surfaces of the six holders 51 to 56. The six recesses 21 to 26 have through holes 21a to 26a, respectively.

As illustrated in FIGS. 12 and 13, the support unit 290 has a recess 291 into which the placement unit 240 is fitted so that the placement unit 240 can be attached and detached. The operator can place the six holders 51 to 56 on the placement unit 240 in the state where the placement unit 240 is detached from the support unit 290. As illustrated in FIG. 13, the placement unit 240 has flanges 10a and 10b, which are used by the operator as holding portions when the operator carries the placement unit 240. In addition, the placement unit 240 has recesses 17 on one outer side surface. The recess 291 of the support unit 290 has protruding portions 77 on one inner side surface. When the placement unit 240 is placed into the support unit 290, the protruding portions 77 are fitted into the recesses 17, and this prevents the operator from attaching the placement unit 240 to the support unit 290 in a wrong orientation.

As illustrated in FIG. 13, the support unit 290 includes a support frame 70, a plate member 40, and displacement members 47. The support frame 70 has an opening 71 in its center, and the plate member 40 is fitted into the opening 71. The paired side surfaces 72 and 73 facing each other of the support frame 70 have six holes 74 and six holes 75, respectively. The plate member 40 has six holes 41 to 46 passing therethrough in the up-down direction. The six holes 41 to 46 are formed at positions that respectively face six holes 21a to 26a formed in the placement unit 240. These six holes 21a to 26a and six holes 41 to 46 are used to detect whether the six holders 51 to 56 are placed on the placement unit 240.

Figure 15A:
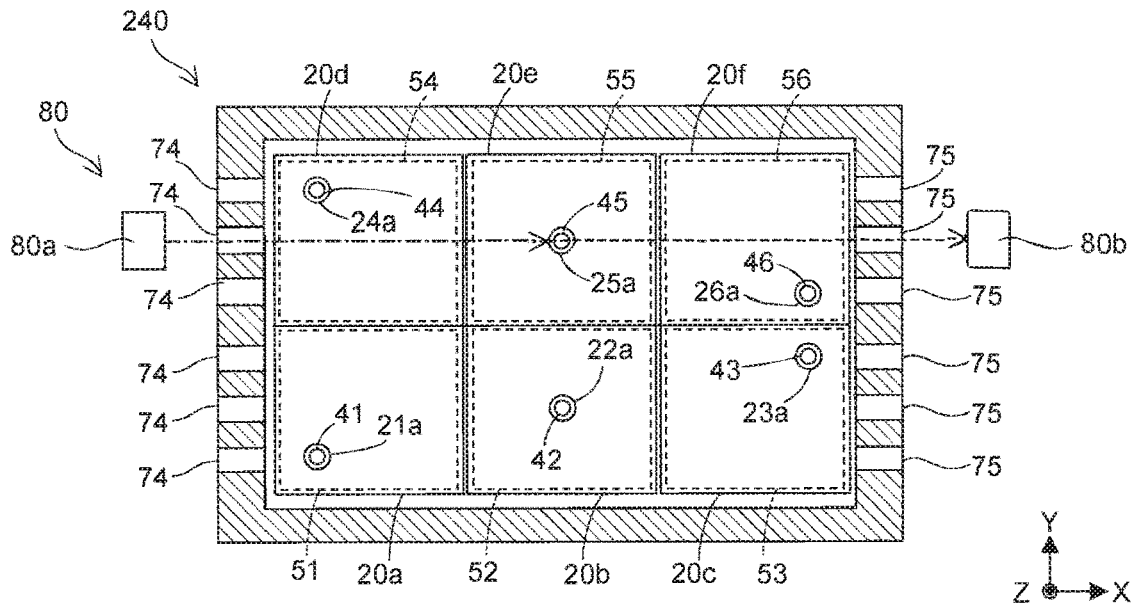
FIGS. 15A, 15B, and 15C each are a schematic diagram illustrating how to detect whether holders according to an embodiment are placed on a placement unit of a measurement apparatus.
Figure 15B:
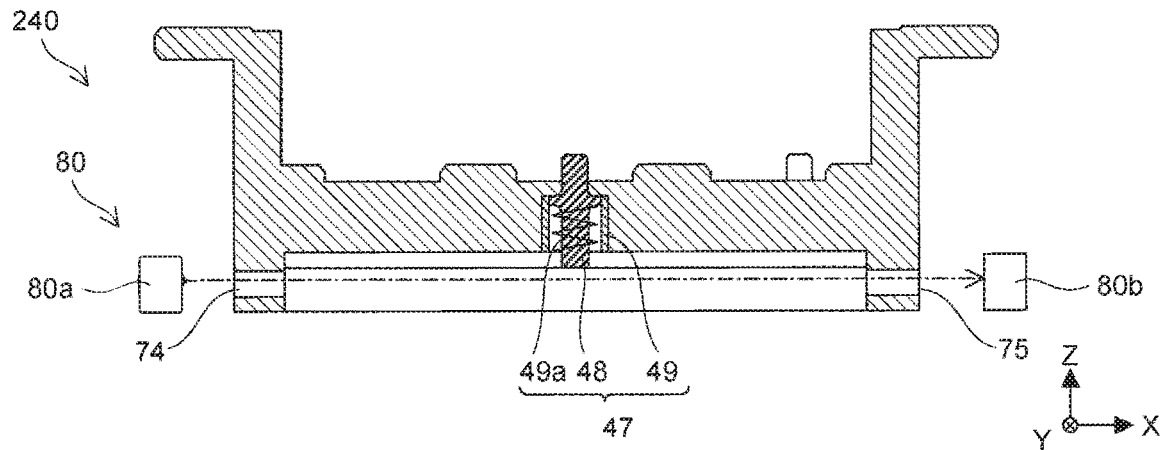
Figure 15C:
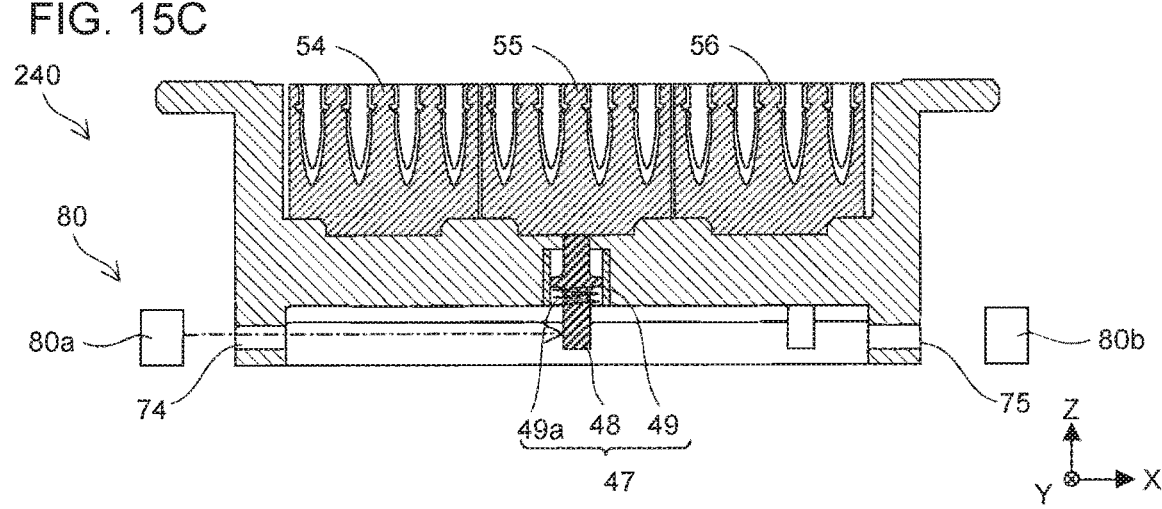

Between the placement unit 240 and the support frame 70 are provided the displacement members 47. Each displacement member 47 has a shaft portion 48 and an outer cylinder 49. The outer cylinder 49 is fixed to the plate member 40. The center portion in the up-down direction of each shaft portion 48 is covered with the outer cylinder 49. The lower end portion of the shaft portion 48 is inserted into each one of the six holes 41 to 46 of the plate member 40, and the upper end portion of the shaft portion 48 is inserted into each one of the six holes 21a to 26a of the placement unit 240. Inside the outer cylinder 49 is inserted an elastic member 49a, as illustrated in FIG. 15B. The shaft portion 48 protrudes upward from the outer cylinder 49, for example, in the state where the holder 51 is not placed on the placement unit 240, as illustrated in FIG. 15B, and when the holder 51 is placed on the placement unit 240, the shaft portion 48, due to the weight of the holder 51, passes through the hole 41 provided in the plate member 40 and moves downward relative to the outer cylinder 49 as illustrated in FIG. 15C.

As illustrated in FIG. 14, the measurement apparatus 200 includes a transfer mechanism 82 including a motor and a rail mechanism and transfers the support unit 290 and the placement unit 240 between the pulling-out position D1 outside the box-shaped part 201 and the reception position D3 inside the box-shaped part 201. The pulling-out position D1 is a position where the operator places the placement unit 240 on the support unit 290. The reception position D3 is a position where the suction unit 271 sucks in specimens after preparation from containers held on the placement unit 240.

The detection unit 80 detects, at the detection position D2 on the way on which the placement unit 240 is transferred from the pulling-out position D1 to the reception position D3, whether the six holders 51 to 56 are placed on the placement unit 240. The detection unit 80 includes a light emitter 80a and a light receiver 80b. The light emitter 80a is an LED, and the light receiver 80b is a light receiving sensor. The light emitter 80a is arranged so as to emit light toward the light receiver 80b.

In the state where the holder is not placed on the placement unit 240 as illustrated in FIG. 15B, the shaft portion 48 of the displacement member 47 does not interrupt light from the light emitter 80a, and light from the light emitter 80a is received by the light receiver 80b. In contrast, in the state where the holder is placed on the placement unit 240 as illustrated in FIG. 15C, the shaft portion 48 of the displacement member 47 interrupts light from the light emitter 80a, and the light receiver 80b does not receive light from the light emitter 80a. In this way, the detection unit 80 can detect the presence of the holders by detecting whether the light receiver 80b receives light. The positions of the displacement member 47 and those of the holes 41 to 46 of the plate member 40 are different from one another in the direction in which the placement unit 240 is transferred, as illustrated in FIG. 15A. This configuration enables the detection unit 80 to detect the presence of each of the holders 51 to 56.

<Processing in Specimen Preparation Apparatus>

Next, processing in the specimen preparation apparatus 100 is described as an example of processing in a specimen preparation apparatus with reference to the flowcharts illustrated in FIGS. 3 and 16.

The controller 107 of the specimen preparation apparatus 100, at a measurement-item-information obtaining step S120, make a request for the measurement items for the blood samples placed on the placement unit 140 to the management apparatus 300 via the measurement apparatus 200 and receives the measurement items. This process corresponds to the process at step S2 illustrated in FIG. 2.

In this process, the controller 107 first associates the position information on the blood samples in the placement unit 140 with the sample IDs. For the convenience of explanation, here it is assumed as illustrated in FIG. 17 that the lateral rows in the holder 51 are called A, B, C, and D in this order, that the longitudinal rows are called 1, 2, 3, and 4 in this order, and that the position information on the positions of a total of 16 holding portions 50 is A-1, A-2, A-3, A-4, B-1, B-2, . . . , D-3, and D-4, based on the positions in the holder 51. Similarly, for the holder 52, it is assumed that the position information on the positions of a total of 16 holding portions 50 is A-5, A-6, A-7, A-8, B-5, B-6, . . . , D-7, and D-8, based on the positions in the holder 51. When the barcode reader 103 of the rack transporter 101 reads a sample ID from the barcode label 2 affixed to a specimen container 5 held in the rack 6, the controller 107 stores the read sample ID into the memory 109, associating the sample ID with the position information from A-1 in order, as illustrated in FIG. 18. The controller 107 transmits the sample IDs to the measurement apparatus 200 via the communication unit 113.

After that, the controller 107 of the specimen preparation apparatus 100 receives measurement items from the measurement apparatus 200 and associates the measurement items with the position information and the sample IDs as illustrated in FIG. 18, and the controller 107 stores these information sets into the memory 109 as order information.

Next, the controller 107 of the specimen preparation apparatus 100 performs the specimen preparation process at steps S121 to S125 which corresponds to the process at step S4 illustrated in FIG. 2.

The controller 107 of the specimen preparation apparatus 100, at step S121, causes the specimen preparation unit 105 to perform processing before heat denaturation on the specimens. Specifically, the controller 107 causes the receiving mechanism 110 to take the specimen containers 5 transported by the rack transporter 101 into the centrifugal reaction unit 130 through the opening 130a and causes the centrifugal reaction unit 130 and the first dispensing mechanism 150 to perform processing of centrifugation, supernatant removal, and reagent dispensing. In this process, the controller 107 determines conditions such as the number of centrifugation operations and the rotation speed as well as the type of reagent to be dispensed according to measurement items included in order information stored in the memory 109.

At step S122, the controller 107 causes the transportation mechanism 190 to transport the holder 51 placed on the placement unit 140 in advance by the operator to the first heater unit 170, and the controller 107 causes the first dispensing mechanism 150 to suck, through the opening 130b, the blood samples subjected to heat denaturation pretreatment and taken into the centrifugal reaction unit 130 and to discharge the blood samples into the containers 7 on the holder 51 transported to the first heater unit 170. In this process, the controller 107 determines containers 7 on the holder 51 into which the blood samples are to be discharged, according to the sets of the sample IDs stored in the memory 109 and the respective position information pieces.

At step S123, the controller 107 causes the first heater unit 170, the second heater unit 180, the centrifugal reaction unit 130, the first dispensing mechanism 150, and the transportation mechanism 190 to perform processing of heating, centrifugation, supernatant removal, and reagent dispensing. With these processes, hybridization occurs between nucleic acids in blood samples and reagents. In these processes, the controller 107 determines conditions such as the number of centrifugation operations and the rotation speed, heating time, and the type of reagent to be dispensed, according to measurement items included in order information stored in the memory 109.

At step S124, the controller 107 causes the first heater unit 170, the second heater unit 180, the centrifugal reaction unit 130, the first dispensing mechanism 150, and the transportation mechanism 190 to perform processing of heating, centrifugation, supernatant removal, and reagent dispensing. With these processes, the substances in the blood sample that interfere with the measurement are removed. In these processes, the controller 107 determines conditions such as the number of centrifugation operations and the rotation speed, heating time, and the type of reagent to be dispensed, according to measurement items included in order information stored in the memory 109.

At step S125, the controller 107 causes the centrifugal reaction unit 130 and the first dispensing mechanism 150 to perform a reagent dispensing process. With this process, the cell nuclei in blood samples are stained. In this process, the controller 107 determines the reagents to be used for staining according to measurement items included in order information stored in the memory 109.

At step S126, the controller 107 transmits, to the measurement apparatus 200, the order information stored in the memory 109 at step S120 on the blood samples for which the specimen preparation process has been completed.

<Processing in Measurement Apparatus>

Figure 19:
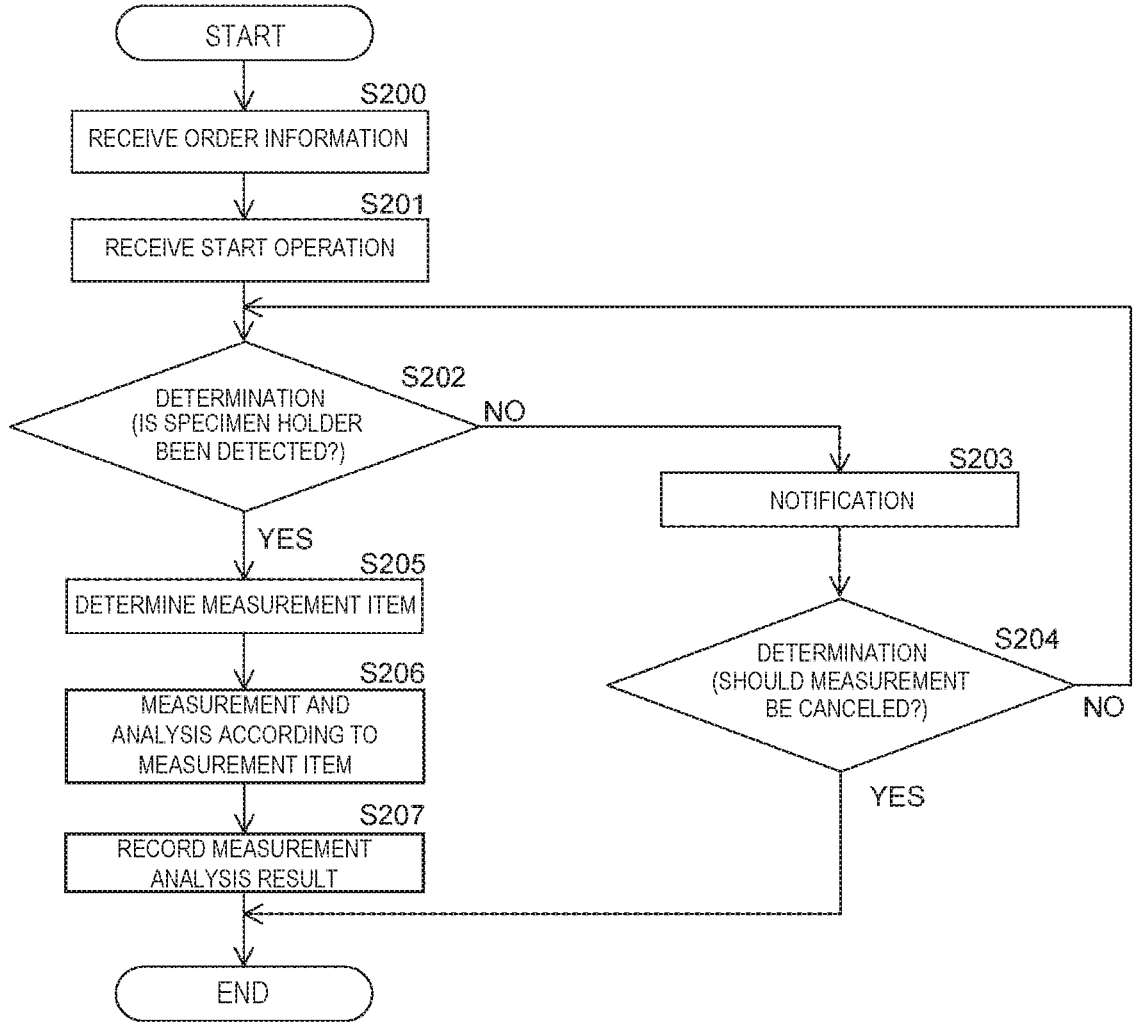
FIG. 19 is a flow diagram illustrating processing performed by a controller of a measurement apparatus according to an embodiment.

Next, processing that the controller 270 of the measurement apparatus 200 performs is described with reference to FIGS. 8 and 10 and a flowchart illustrated in FIG. 19. First, the controller 270, at step S200, receives the order information transmitted from the controller 107 of the specimen preparation apparatus 100 at step S126 illustrated in FIG. 16 and stores it into the memory 274. This process corresponds to the process at step S6 illustrated in FIG. 2. The controller 270 receives order information also from the specimen preparation apparatuses 100a and 100b, integrates it as illustrated in FIG. 20, and stores the integrated information into the memory 274.

At step S201 the controller 270 receives a measurement start instruction by the operator via the operation unit 272. At step S202, the controller 270 determines whether the holder 51 is detected by the detection unit 80.

If the holder 51 is detected (YES at step S202), the process proceeds to step S205, and if the holder 51 is not detected (NO at step S202), the process proceeds to step S203. At step S203, the controller 270 causes the display 273 to display an indication meaning that the holder 51 is not placed properly. Note that the way of the notification that the holder 51 is not placed properly is not limited to displaying on the display 273, but for example, the notification may be made by sounding an alarm. At step S204, the controller 270 determines whether to stop the measurement. Specifically, at step S204, the controller 270 causes the display 273 to display a screen for selecting continuing the measurement or canceling the measurement. If the operator selects desiring to continue the measurement (NO at step S204), the process returns to step S202, and if the operator selects canceling the measurement (YES at step S204), the process ends.

If the holder 51 is detected at step S202 (YES at step S202), the controller 270, at step S205, reads order information stored in the memory 274 and determines the measurement items corresponding to the position information on the holder detected by the detection unit 80, as the measurement items for the specimens for measurement.

At step S206, the controller 270 causes the measurement unit 280 to measure the specimens, analyzes the obtained optical information, and obtains the analysis results. In this analysis process, the controller 270 uses an analysis algorithm according to the measurement items included in the order information.

At step S207, the controller 270 enters the obtain analysis results into the fields for measurement analysis results illustrated in FIG. 20 and stores them into the memory 274, and then the controller 270 ends the process.

As has been described above, since the adapters 120a to 120f of the specimen preparation apparatuses 100, 100a, and 100b each have a shape corresponding to a specific holder of the holders 51 to 56, it is possible to prevent misplacement of the adapters 120a to 120f without complicating the structure and thereby prevent specimens being from prepared by a method different from the method desired by the operator.

Also, since the adapters 20a to 20f of the measurement apparatus 200 each have a shape corresponding to a specific holder of the holders 51 to 56, it is possible to prevent misplacement of the adapters 120a to 120f without complicating the structure and thereby making it possible to process specimens by the method desired by the operator.

[Modification 1]

Figure 21A:
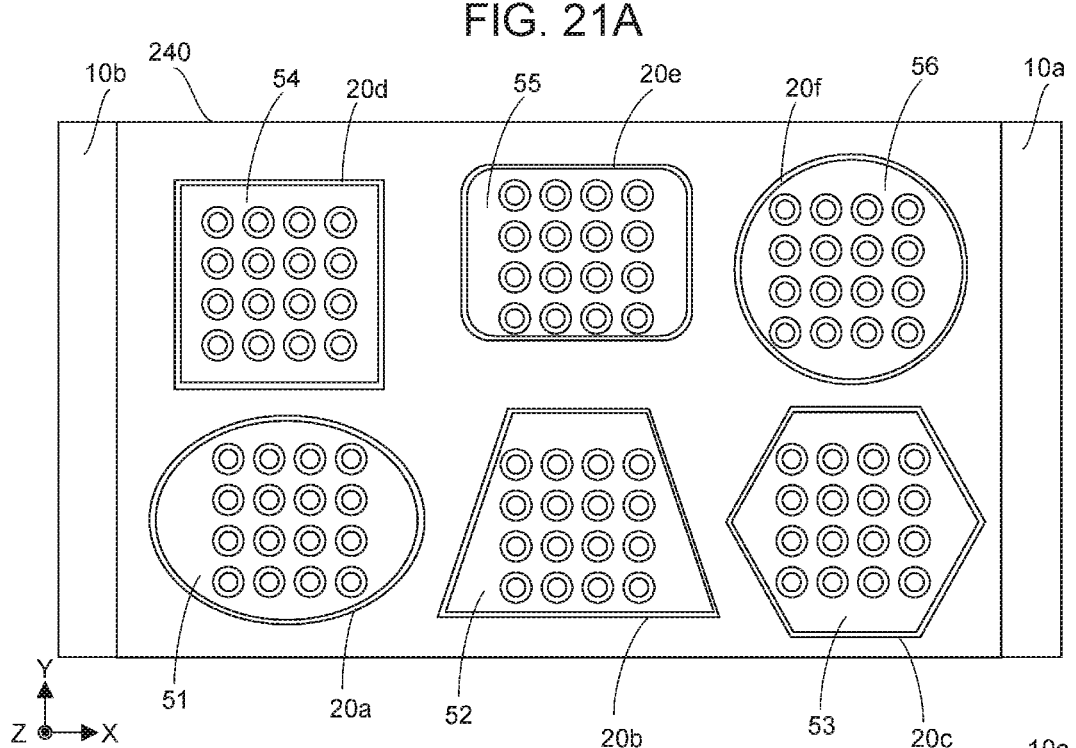
FIG. 21A is a plan view diagram illustrating shapes of holders and a shape of a placement unit according to modification 1.

Instead of providing the engagement portions 61 in the six holders 51 to 56, the overall shapes of the six holders 51 to 56 may be different shapes, for example, elliptical shapes, polygonal shapes, and rhombic shapes, as illustrated in FIG. 21A. Also, in this case, the adapters 20a to 20f of the placement unit 240 each have a shape corresponding to a specific holder of the holders 51 to 56. The operator can easily understand visually that the shapes of the six holders 51 to 56 are different, and this reliably prevents misplacement of the six holders 51 to 56 into the placement unit 240.

[Modification 2]

Figure 21B:
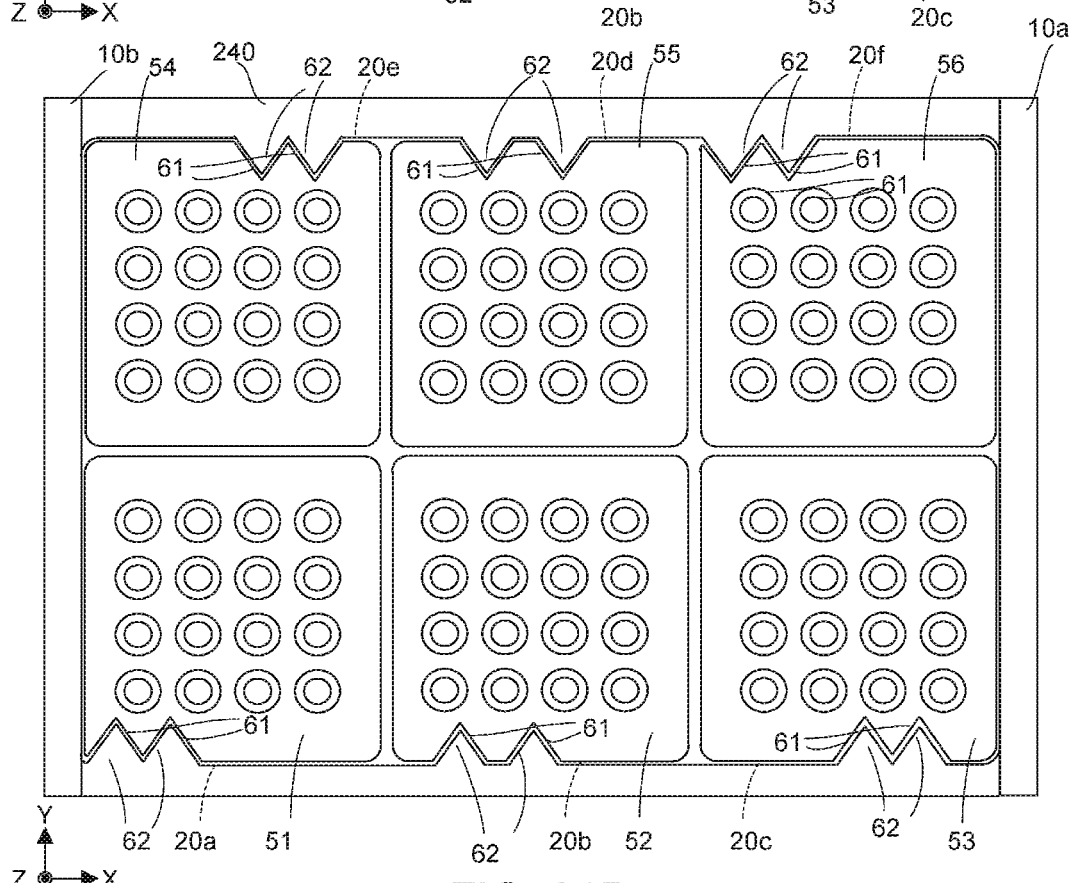
FIG. 21B is a plan view diagram illustrating shapes of holders and a shape of a placement unit according to modification 2.

As illustrated in FIG. 21B, the number of engagement portions 61 and engagement portions 62 provided in each holder and adapter may be plural. Also, in this case, the adapters 20a to 20f of the placement unit 240 each have a shape corresponding to a specific holder of the holders 51 to 56.

Although embodiments described above is based on an example of performing measurement on blood, the configuration may be used for measurement on specimens other than blood, for example, urine. In addition, the specimen preparation apparatus, the measurement apparatus, and the management apparatus may be connected with one another as appropriate via a dedicated line, a general-purpose network, a public network, or the like. In addition, the measurement apparatus may also serve as a management apparatus or a specimen preparation apparatus.

Although in the above embodiments, the measurement apparatus obtains the measurement items for specimens from the management apparatus, the operator may directly input the measurement items for specimens via an input unit of the measurement apparatus. Alternatively, the measurement apparatus may obtain measurement items by reading information stored in a storage medium such as a CD-ROM.

Although in the above embodiments, all the six holders 51 to 56 have shapes different from one another, some of the holders may have the same shape. Similarly, although in the above embodiments, all the six adapters 20a to 20f of the placement unit 240 in the measurement apparatus 200 have shapes different from one another, some of the adapters may have the same shape. For example, a configuration may be in such a way that the holder 52 is replaced with the holder 51 and two holders 51 are used, and that at the same time, the adapter 20b is replaced with the adapter 20a and two adapters 20a are provided. In this case, the two holders 51 can be identified by adding marking or coloring the holders, attaching IC chips storing identification information to the holders, or other methods.

In addition, although in the above embodiments, the adapters 120b to 120f have the inner periphery shapes that are the same as the outer periphery shapes of the holders 51 to 56, the present disclosure is not limited to this example as long as the shapes of the adapters that fit the shapes of the holders. For example, the holder 51 may have two or more engagement portions 61. In this case, one engagement portion 61 is formed at the position where it is engaged with the engagement portion 62 of the adapter 120a as described above, and the other engagement portion 61 is formed at a position where it is not engaged with any of the engagement portions 62 of the adapters 120b to 120f.

The invention claimed is:

1. A specimen processing apparatus for performing processing on a specimen contained in a container, comprising:

holders having different shapes, each of the holders being configured to hold the container, wherein each of the holders has a same outline in a plan view except that each of the holders has an engagement portion provided at the outline such that the engagement portions of the holders are provided at different positions from one another or are provided in different shapes from one another in the plan view;

a holder placement unit that comprises holder receiving portions recessed in the holder placement unit, the shapes of the holder receiving portions corresponding to the shapes of the holders in the plan view, wherein each of the holders is configured to be received and fitted in a respective one of the holder receiving portions in a specific orientation with respect to the corresponding shapes of the respective holder and the respective holder receiving portion and wherein each of the holder receiving portions has a same outline in a plan view except that each of the holder receiving portions has an engagement portion provided at the outline such that the engagement portions of the holder receiving portions are provided at different positions from one another or are provided in different shapes from one another in the plan view; and a specimen processing unit that is configured to perform processing on the specimen contained in the container held by one of the holders placed on the holder placement unit.

2. The specimen processing apparatus according to claim 1, further comprising a holder detector that is configured to detect the holder being placed on the holder placement unit.

3. The specimen processing apparatus according to claim 2, further comprising a controller that is configured to, in response to the holder detector detecting that the holder is placed on the holder placement unit, control the specimen processing unit to perform processing on the specimen contained in the detected holder.

4. The specimen processing apparatus according to claim 3, further comprising a start-instruction reception unit that is configured to receive an instruction to start processing on the specimen, wherein the controller is configured to prohibit the specimen processing unit from performing processing on the specimen, in response to detecting that the holder is not placed on the holder placement unit after the start-instruction reception unit receives the instruction to start processing on the specimen.

5. The specimen processing apparatus according to claim 4, further comprising a notification unit, wherein the controller is configured to control the notification unit to provide a notification, in response to detecting that the holder is not placed on the holder placement unit after the start-instruction reception unit receives the instruction to start processing on the specimen.

6. The specimen processing apparatus according to claim 1, further comprising a support unit that is configured to detachably support the holder placement unit.

7. The specimen processing apparatus according to claim 6, wherein the support unit has a shape to receive the holder placement unit only in a specified orientation.

8. The specimen processing apparatus according to claim 1, further comprising:
 a memory that stores order information on the specimen contained in the container held by the holder placed on the holder placement unit; and
 a controller that is configured to control the specimen processing unit based on the order information.

9. A specimen measurement system comprising:
 a specimen preparation apparatus that is configured to prepare a specimen using a reagent; and
 a measurement apparatus that is configured to measure a specimen prepared by the specimen preparation apparatus, wherein
 the specimen preparation apparatus is configured to prepare the specimen in a container, and
 the measurement apparatus comprises:
  holders having different shapes, each of the holders being configured to hold the container, wherein each of the holders has a same outline in a plan view except that each of the holders has an engagement portion provided at the outline such that the engagement portions of the holders are provided at different positions from one another or are provided in different shapes from one another in the plan view;
  a holder placement unit that comprises holder receiving portions recessed in the holder placement unit, the shapes of the holder receiving portions corresponding to the shapes of the holders in the plan view, wherein each of the holders is configured to be received and fitted in a respective one of the holder receiving portions in a specific orientation with respect to the corresponding shapes of the respective holder and the respective holder receiving portion and wherein each of the holder receiving portions has a same outline in a plan view except that each of the holder receiving portions has an engagement portion provided at the outline such that the engagement portions of the holder receiving portions are provided at different positions from one another or are provided in different shapes from one another in the plan view; and
  a specimen processing unit that is configured to perform processing on the specimen contained in the container held by one of the holders placed on the holder placement unit.

\* \* \* \* \*